US011027047B2

(12) United States Patent
Hingtgen et al.

(10) Patent No.: US 11,027,047 B2
(45) Date of Patent: Jun. 8, 2021

(54) DELIVERY VEHICLES FOR STEM CELLS AND USES THEREOF

(71) Applicant: The University of North Carolina at Chapel Hill, Chapel Hill, NC (US)

(72) Inventors: Shawn D. Hingtgen, Chapel Hill, NC (US); Julio Rodriguez Bago, Chapel Hill, NC (US); Matthew G. Ewend, Chapel Hill, NC (US); Karen J. Giroux, Chapel Hill, NC (US); Raluca Dumitru, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 15/559,596

(22) PCT Filed: Mar. 30, 2016

(86) PCT No.: PCT/US2016/024896
§ 371 (c)(1),
(2) Date: Sep. 19, 2017

(87) PCT Pub. No.: WO2016/160918
PCT Pub. Date: Oct. 6, 2016

(65) Prior Publication Data
US 2018/0064854 A1 Mar. 8, 2018

Related U.S. Application Data

(60) Provisional application No. 62/140,820, filed on Mar. 31, 2015.

(51) Int. Cl.
*A61L 27/58* (2006.01)
*A61L 27/22* (2006.01)
(Continued)

(52) U.S. Cl.
CPC ............ *A61L 27/58* (2013.01); *A61L 27/222* (2013.01); *A61L 27/3834* (2013.01);
(Continued)

(58) Field of Classification Search
None
See application file for complete search history.

(56) References Cited

U.S. PATENT DOCUMENTS

| 5,512,301 A | 4/1996 | Song et al. |
| 5,851,832 A | 12/1998 | Weiss et al. |

(Continued)

FOREIGN PATENT DOCUMENTS

| CN | 103068974 | 4/2013 |
| CN | 103561788 | 2/2014 |

(Continued)

OTHER PUBLICATIONS

Bensaid et al., Biomaterials 24: 2497-2502 (2003).*
(Continued)

*Primary Examiner* — Erin M. Bowers
(74) *Attorney, Agent, or Firm* — Myers Bigel, P.A.

(57) ABSTRACT

Provided herein according to some embodiments is a biocompatible scaffold comprising stem cells (e.g., a pliable scaffold) suitable for intracavity administration after surgical removal of a tumor, wherein the scaffold allows the stem cells to migrate away from the scaffold and towards a cancerous or damaged tissue, wherein the stem cells are loaded with a therapeutic agent and/or a reporter molecule. Methods of forming the scaffold, and methods of use thereof, are also provided.

9 Claims, 24 Drawing Sheets

(51) Int. Cl.

| | |
|---|---|
| *A61L 27/38* | (2006.01) |
| *A61L 27/54* | (2006.01) |
| *A61L 27/56* | (2006.01) |
| *A61L 27/50* | (2006.01) |
| *C12N 5/0793* | (2010.01) |
| *C12N 5/0775* | (2010.01) |
| *C12N 5/00* | (2006.01) |
| *A61L 31/16* | (2006.01) |

(52) U.S. Cl.
CPC .......... *A61L 27/3878* (2013.01); *A61L 27/50* (2013.01); *A61L 27/54* (2013.01); *A61L 27/56* (2013.01); *A61L 31/16* (2013.01); *C12N 5/0012* (2013.01); *C12N 5/0619* (2013.01); *C12N 5/0663* (2013.01); *C12N 2501/602* (2013.01); *C12N 2502/1352* (2013.01); *C12N 2506/1307* (2013.01); *C12N 2510/00* (2013.01); *C12N 2513/00* (2013.01); *C12N 2533/56* (2013.01); *C12N 2535/00* (2013.01)

(56) References Cited

U.S. PATENT DOCUMENTS

| | | | |
|---|---|---|---|
| 6,056,970 | A | 5/2000 | Greenawalt et al. |
| 6,087,168 | A | 7/2000 | Levesque et al. |
| 6,699,484 | B2 | 3/2004 | Whitmore et al. |
| 7,524,489 | B2 | 4/2009 | Messina et al. |
| 8,048,446 | B2 | 11/2011 | Lelkes et al. |
| 8,338,176 | B2 | 12/2012 | Daadi et al. |
| 8,475,812 | B2 | 7/2013 | Nur et al. |
| 8,673,923 | B2 | 3/2014 | El-Deiry et al. |
| 8,785,187 | B2 | 7/2014 | Conti et al. |
| 8,815,589 | B2 | 8/2014 | Huang et al. |
| 2009/0105671 | A1 | 4/2009 | Daggar et al. |
| 2009/0175826 | A1 | 7/2009 | Subbiah et al. |
| 2009/0203671 | A1 | 8/2009 | Glaser et al. |
| 2010/0021437 | A1 | 1/2010 | Isacson et al. |
| 2011/0250684 | A1 | 10/2011 | Akamatsu et al. |
| 2011/0296542 | A1 | 12/2011 | Wang et al. |
| 2012/0134968 | A1* | 5/2012 | Wang ............... A61L 27/58 424/93.7 |
| 2012/0269778 | A1 | 10/2012 | Huang et al. |
| 2014/0051171 | A1 | 2/2014 | Christensen et al. |
| 2014/0065227 | A1 | 3/2014 | Isacson et al. |
| 2014/0086907 | A1 | 3/2014 | Shah |
| 2014/0308256 | A1 | 10/2014 | Lu et al. |

FOREIGN PATENT DOCUMENTS

| | | | |
|---|---|---|---|
| CN | 103740757 | | 4/2014 |
| EP | 1022331 | | 5/2002 |
| EP | 1466633 | A1 | 10/2004 |
| EP | 1775340 | | 4/2007 |
| EP | 2821481 | | 1/2015 |
| EP | 2670426 | | 5/2017 |
| JP | 2009519042 | | 5/2009 |
| KR | 101272901 | | 11/2013 |
| WO | 1994/016718 | | 8/1994 |
| WO | 2001/008691 | | 2/2001 |
| WO | WO 03/026489 | A2 | 4/2003 |
| WO | 2009/148488 | | 12/2009 |
| WO | 2010/108126 | | 9/2010 |
| WO | 2011/035030 | | 3/2011 |
| WO | 2012/022725 | | 2/2012 |
| WO | WO 2012/022725 | * | 2/2012 |
| WO | 2012/118988 | | 3/2012 |
| WO | 2012/100083 | | 7/2012 |
| WO | 2012/106281 | | 8/2012 |
| WO | WO 2012/106281 | * | 8/2012 |
| WO | 2013/124309 | | 8/2013 |
| WO | 2013/124816 | | 8/2013 |
| WO | 2013/188748 | | 12/2013 |
| WO | 2014/018113 | | 1/2014 |
| WO | 2014/035474 | | 3/2014 |
| WO | 2014/066297 | | 5/2014 |
| WO | WO 2014/127232 | * | 8/2014 |
| WO | 2014/163425 | | 10/2014 |
| WO | 2016/141162 | | 9/2016 |
| WO | 2016/160918 | | 10/2016 |

OTHER PUBLICATIONS

Lu et al., Cell 150: 1264-1273 (2012).*
https://en.wikipedia.org/wiki/Thrombin, accessed Mar. 19, 2020.*
Lim et al., Biomaterials 33: 3446-3455 (2012).*
Zhong et al., J. R. Soc. Interface 5: 957-975 (2008).*
Bao-Ling et al "Graft of the gelatin sponge scaffold containing genetically-modified neural stem cells promotes cell differentiation, axon regeneration, and functional recovery in rat with spinal cord transection" Journal of Biomedical Materials Research, 103A(4):1533-1545 (2015).
Database BIOSIS: Biosciences Information Service, Nakamura et al. "Transplantation of neural stem cells promote axonal growth and functional recovery after spinal cord injury in neonatal rats" 27(1):962 (2001).
Database MEDLINE: US Nabonal Library of Medicine, Chen et al. "Neurotrohpin-3 stimulates migration of mesenchymal stem cells Overexpressing TrkC" Current Medicinal Chemistry, 20(24):3022-3033 (2013).
European Search Report corresponding to European Patent Application No. 16774062.0, dated Oct. 29, 2018, 12 pages.
International Search Report and Written Opinion, PCT/US2016/024896, dated Aug. 14, 2016.
Singh D et al. Proliferation of myoblast skeletal cells on three-dimensional supermacroporous cryogels. International Journal of Biological Sciences. 2010; 6(4): 371-381.
Zhang M et al. Pharmacological reprogramming of fibroblasts into neural stem cells by signaling-directed transcriptional activation. Cell Stem Cell. May 5, 2016; 18: 653-687.
European Search Report and Opinion, EP16759479, dated Jul. 18, 2018, 6 pages.
Onorati M et al. Neuropotent self-renewing neural stem (NS) cells derived from mouse induced pluripotent stem (iPS) cells, Molecular and Cellular Neuroscience. 2010; 43: 297-295.
Bago Jr et al. "Neural stem cell therapy for cancer" Methods (http://dx.doi.org/10.1016/j.ymeth.2015.08.013. 7 pp (2015).
Bago Jr et al. Therapeutically engineered induced neural stem cells are tumour-homing and inhibit progression of glioblastoma. Nature Communications. Feb. 2, 2016; 7:10593; 1-13.
Bago Jr et al. Tumor-homing cytotoxic human induced neural stem cells for cancer therapy. Science Translational Medicine. Feb. 1, 2017; 9: 1-13.
Castano J et al. Fast and Efficient Neural Conversion of Human Hematopoietic Cells. Stem Cell Reports. Dec. 9, 2014; 3(6): 1118-1131.
International Search Report and Written Opinion, PCT/US2016/020649, dated Jun. 30, 2016.
Kauer TM et al. Encapsulated therapeutic stem cells implanted in the tumor resection cavity induce cell death in gliomas. Nat Neurosci. Dec. 25, 2011; 15(2): 197-204.
Lujan E et al. Direct conversion of mouse fibroblasts to self-renewing, tripotent neural precursor cells. PNAS. Feb. 14, 2012; 109(7): 2527-2532.
Matsui T et al. Neural stem cells directly differentiated from partially reprogrammed fibroblasts rapidly acquire gliogenic competency. Stem Cells. 2012; 30: 1109-1119.
Ring KL et al. Drect reprogramming of mouse and human fibroblasts into multipotent neural stem cells with a single factor. Cell Stem Cell. Jul. 6, 2012; 11: 100-109.
Thier M et al. Direct conversion of fibroblasts into stably expandable neural stem cells. Cell Stem Cell. Apr. 6, 2012; 10: 437-479.
Extended Europeen Search Report, European Patent Application No. 16759479, dated Jul. 20, 2018, 7 pages.
Xi G. et al., Induced Neural Stem Cells Generated from Rat Fibroblasts, Genomics Proteomics Bioinformatics , Sep. 27, 2013, vol. 11, No. 5, pp. 312-319.

(56) References Cited

OTHER PUBLICATIONS

Alfonso-Pecchio A. et al., Therapeutically engineered induced neural stem cells are tumor-homing and inhibit progression of glioblastorna. Neuro-Oncology, Nov. 7, 2014, vol. 16, No. SUPPL, 5. Abstract.
Kim, S.U. "Neural stem cell-based gene therapy for brain tumors" Stem Cell Rev., Mar. 7, 2011, vol. 7, No. 1, pp. 130-140, Abstract.
Search Report and Written Opinion, Singapore Application No. 11201707047V, dated Aug. 20, 2018, 10 pages.
Ries et al. "Human Mesenchymal Stem Cell Transdifferentiation to Neural Cells: Role of Tumor Necrosis Factor Alpha," Stem Cells and Cancer Stem Cells, 8:71-78 (2012) Abstract only.
Notification Concerning Transmittal of International Preliminary Report on Patentability (Chapter I of the Patent Cooperation Treaty) PCT/US2016/020649, dated Sep. 14, 2017 (6 pages).
Notification Concerning Transmittal of International Preliminary report on Patentability (Chapter I of the Patent Cooperation Treaty), PCT/US2016/024896, dated Oct. 12, 2017 (8 pages).
Aboody et al. "Stem and progenitor cell-mediated tumor selective gene therapy." Gene Therapy, 15:739-752 (2008).
Aboody et al. "Neural stem cell-mediated enzyme/prodrug therapy for glioma: preclinical studies," Science Translational Medicine, 5, 13 pages (2013).
Ahmed et al. "The use of neural stem cells in cancer gene therapy: predicting the path to the clinic," Current Opinion in Molecular Therapeutics, 12:546-552 (2010).
Bagci-Onder et al. "Real-time imaging of the dynamics of death receptors and therapeutics that overcome TRAIL resistance in tumors," Oncogene, 6;32(23):2818-27 (2013).
Gelfoam® absorbable gelatine compressed sponge, USP. Physician Prescribing Information, Pfizer, Inc. Retrieved from the internet Aug. 29, 2018.

Han D. W. et al., Direct reprogramming of fibroblasts into neural stem cells by defined factors. Cell Stem Cell., vol. 10, No. 4, pp. 465-472, Mar. 22, 2012.
Hingtgen et al. "Targeting multiple pathways in gliomas with stem cell and viral delivered S-TRAIL and Temozolomide," Mol Cancer Ther. 7(11):3575-85 (2008).
Ivanov et al. "A role for TRAIL/TRAIL-R2 in radiation-induced apoptosis and radiation-induced bystander response of human neural stem cells," Apoptosis. 19(3):399-413 (2014).
Sasportas et al. "Assessment of therapeutic efficacy and fate of engineered human mesenchymal stem cells for cancer therapy," PNAS 106(12):4822-7 (2009).
STEMdiff SMADi Neural Induction Kit, medium and supplement product informatioon sheet. STEMCELL Technologies, Copyright 2017, Retrieved from the internet Aug. 29, 2018.
STEMdiff Neural Progenitor Medium, product information sheet, STEMCELL Technologies, Copyright 2016. Retrieved from the internet Aug. 29, 2018.
TISSEEL Fibrin Sealant Physician Prescribing Information, Baxter Healthcare Corporation, Retrieved from the internet Aug. 29, 2018.
Chinese Office Action corresponding to CN 201680019879.1, dated Nov. 28, 2019 (29 pp, including English translation).
Japanese Office Action corresponding to JP 2017-550734; dated Jan. 24, 2020 (9 pages, including English translation).
European Search Report corresponding to EP16774062.0, dated Oct. 4, 2019 (6 pp).
Wang et al. "The role of stiffness of gelatin—hydroxyphenylpropionic acid hydrogels formed by enzyme-mediated crosslinking on the differentiation of human mesenchymal stem cell" Biomaterials, 31(33):8608-8616 (2010).

\* cited by examiner

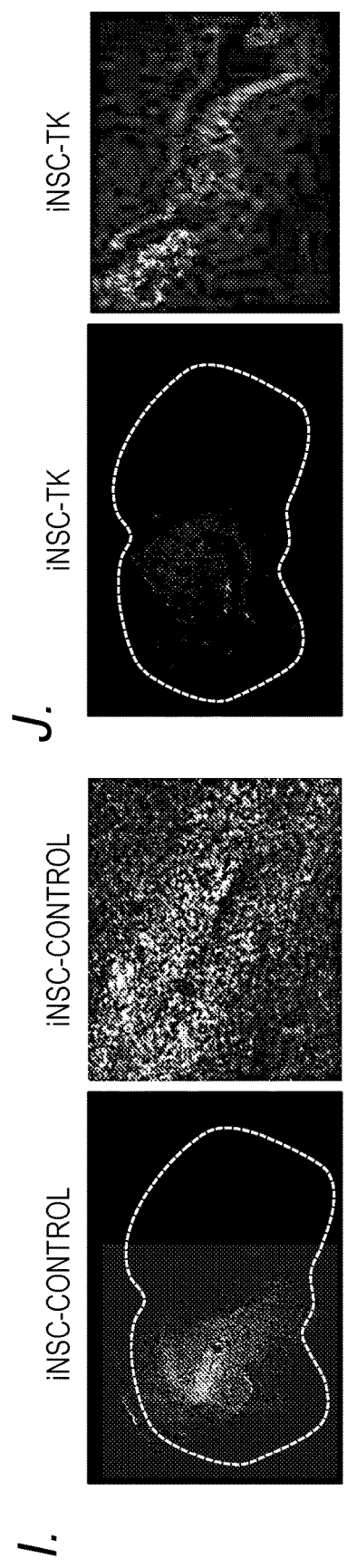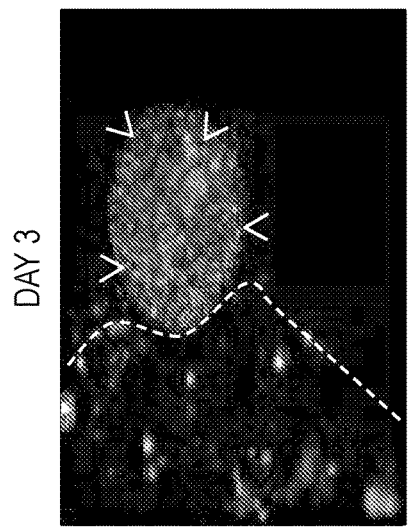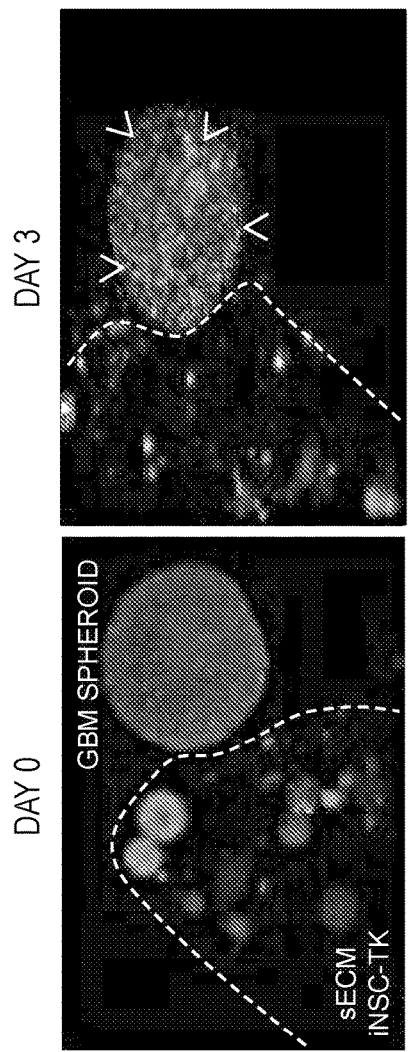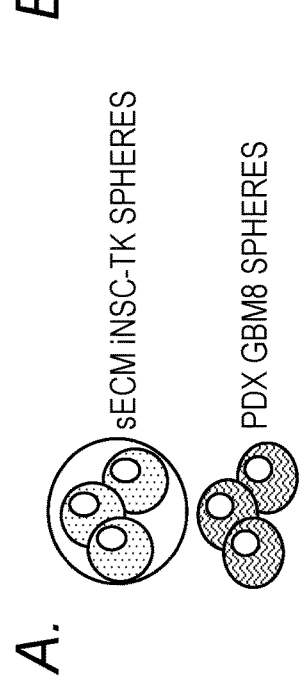
FIG. 5
FIG. 6

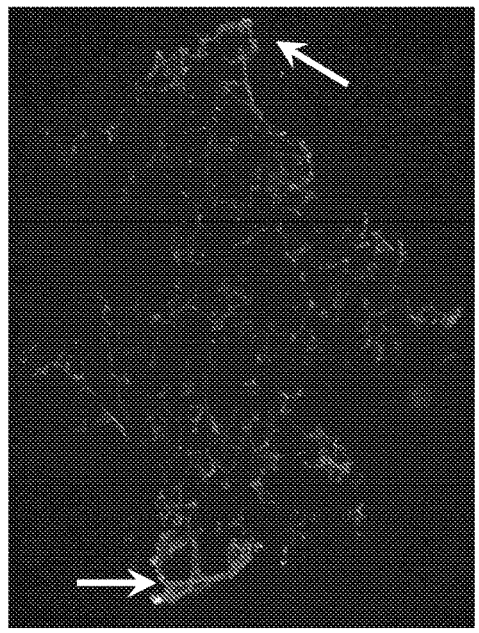
FIG. 12
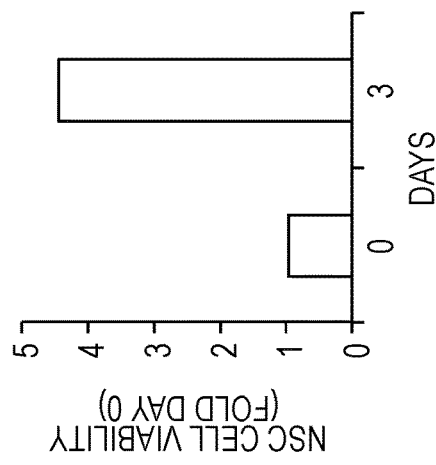
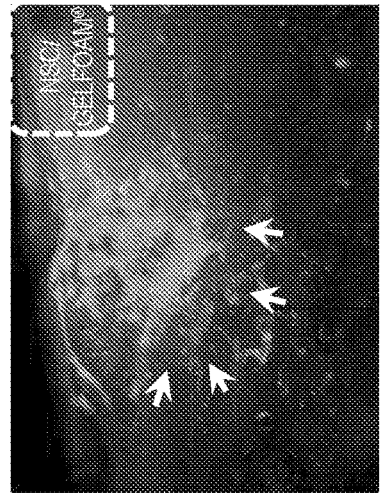
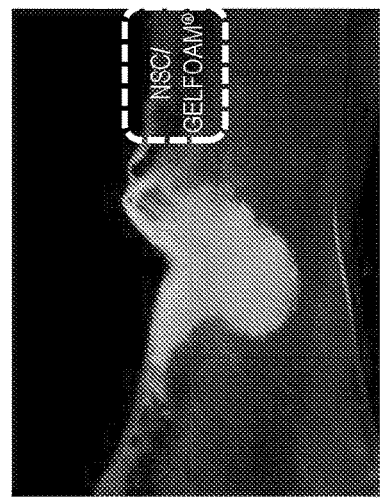
FIG. 13
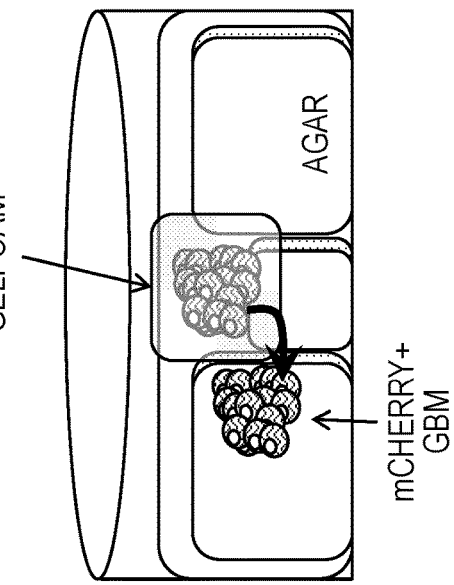

DELIVERY VEHICLES FOR STEM CELLS AND USES THEREOF

RELATED APPLICATIONS

This application is a 35 U.S.C. § 371 national phase entry of PCT Application PCT/US2016/024896, filed Mar. 30, 2016, and published in English on Oct. 6, 2016, as International Publication No. WO 2016/160918, and which claims the benefit of U.S. Provisional Patent Application Ser. No. 62/140,820, filed Mar. 31, 2015, the disclosure of each of which is incorporated by reference herein in its entirety.

BACKGROUND

Glioblastoma (GBM) is the most common primary brain cancer, and one of the deadliest tumors. Adamson, C. et al. Glioblastoma multiforme: a review of where we have been and where we are going. *Expert Opin Investig Drugs* 18, 1061-1083 (2009); Erpolat, O. P. et al. Outcome of newly diagnosed glioblastoma patients treated by radiotherapy plus concomitant and adjuvant temozolomide: a long-term analysis. *Tumori* 95, 191-197 (2009). Invasive GBM cells escape into the non-diseased brain, making complete surgical resection impossible, and small molecule chemotherapies are unable to reach invasive GBM foci. As a result, GBM is incurable, and median survival remains 12-15 months. Stupp, R. et al. Effects of radiotherapy with concomitant and adjuvant temozolomide versus radiotherapy alone on survival in glioblastoma in a randomised phase III study: 5-year analysis of the EORTC-NCIC trial. *The lancet oncology* 10, 459-466 (2009).

Engineered stem cell (SC) therapies are a promising treatment strategy for GBM. Aboody, K. S. et al. Stem and progenitor cell-mediated tumor selective gene therapy. *Gene therapy* 15, 739-752 (2008); Ahmed, A. U. et al. The use of neural stem cells in cancer gene therapy: predicting the path to the clinic. *Current opinion in molecular therapeutics* 12, 546-552 (2010). SCs have the unique ability to seek out GBM, migrating to solid and diffuse GBM deposits. When genetically engineered with cytotoxic agents, SCs deliver therapies that eradicate solid GBM in a variety of preclinical studies. However, surgical resection is part of the standard of care for GBM patients, and the first clinical trial for SC-therapy of GBM is being tested in post-surgical patients. Aboody, K. S. et al. Neural stem cell-mediated enzyme/prodrug therapy for glioma: preclinical studies. *Science translational medicine* 5 (2013).

Creating a delivery vehicle that addresses the unique demands of cytotoxic SC therapy and is also compatible with human patient testing and treatment is a new and critical challenge.

SUMMARY

Provided herein according to some embodiments is a method of forming a scaffold (e.g., a pliable scaffold) comprising stem cells (e.g., human stem cells), wherein said stem cells are loaded with a therapeutic agent and/or a reporter molecule. In some embodiments, the method includes: providing a scaffold material, optionally wherein the scaffold is biocompatible, and optionally wherein said scaffold is biodegradable and/or bioabsorbable, and loading said stem cells onto said scaffold. In some embodiments, the scaffold is suitable for intracavity administration after surgical removal of a tumor (e.g., brain tumor). In some embodiments, the scaffold is provided as a sterile scaffold.

In some embodiments, the scaffold includes a polymerized and/or crosslinked material selected from polyanionic polysaccharides (e.g., hyaluronic acid (HA), carboxymethylcellulose (CMC), carboxymethylamylose (CMA), chondroitin-6-sulfate, dermatin sulfate, dermatin-6-sulfate and combinations thereof), alginic acid, chitin, chitosan, fibrin, dextran, polylactic acid, polyglycolic acid, poly(D−)lactic acid, polyglycoliclactic acid, keratin, laminin, elastin, collagen and other naturally-occurring extracellular matrix proteins, gelatin, polydioxanones, polycaprolactone, and blends and co-polymers thereof.

In some embodiments, the scaffold comprises a bioabsorbable gelatin sponge.

In some embodiments, the cells are mesenchymal stem cells or neural stem cells. In some embodiments, the stem cells are induced neural stem cells. In some embodiments, the stem cells are induced neural stem cells derived from somatic cells such as a skin fibroblast cells (e.g., by rapid transdifferentation).

In some embodiments, the therapeutic agent is a protein toxin, an oncolytic virus, a pro-apoptotic agent, or an enzyme useful for enzyme/prodrug therapy.

Also provided is a method of forming a scaffold comprising stem cells (e.g., human stem cells), wherein said stem cells are loaded with a therapeutic agent and/or a reporter molecule. In some embodiments, the method includes: providing a polymerizable and/or crosslinkable material, optionally wherein the material is sterile, mixing the polymerizable and/or crosslinkable material with said stem cells to form a mixture of the material and stem cells, and polymerizing and/or crosslinking said material of said mixture, to thereby form said scaffold comprising stem cells.

In some embodiments, the scaffold is biocompatible and allows the stem cells to migrate away from the scaffold and towards a cancerous or damaged tissue. In some embodiments, the polymerizing and/or crosslinking are performed in situ during intracavity administration after surgical removal of a brain tumor. In some embodiments, the scaffold is administered to line the walls of a resection cavity of the brain tumor.

Further provided is a delivery vehicle, comprising: a pliable biocompatible scaffold; and a stem cell (e.g., human stem cell) incorporated in said scaffold, wherein said stem cell is loaded with a therapeutic agent and/or a reporter molecule.

In some embodiments, the stem cell is a mesenchymal stem cell or a neural stem cell. In some embodiments, the stem cell is an induced neural stem cell. In some embodiments, the stem cell is an induced neural stem cell derived from a somatic cell such as a skin fibroblast cell (e.g., by rapid transdifferentation).

In some embodiments, the therapeutic agent is a protein toxin, an oncolytic virus, a pro-apoptotic agent, or an enzyme useful for enzyme/prodrug therapy.

Also provided is a method of treating a brain cancer in a subject in need thereof, comprising administering a delivery vehicle comprising a stem cell as taught herein to said subject.

In some embodiments, the stem cell is allogeneic or autologous with respect to the subject. In some embodiments, the stem cell is a human induced neural stem cell autologous with respect to said subject, and the administering is carried out 1, 2, 3 or 4, to 7, 10, 14 or 21 days, after said providing the somatic cell.

In some embodiments, the stem cell (or a progeny thereof of proliferating stem cells) is maintained in the area of treatment for at least 15, 20, 30, or 40 days after the administration.

Further provided is the use of a delivery vehicle comprising a stem cell as taught herein in a method of treating a brain cancer in a subject in need thereof.

BRIEF DESCRIPTION OF THE DRAWINGS

FIG. 13. In vitro 3-dimensional migration analysis. (A) Schematic representation of the strategy. Culture plates are filled with agar and mCherry+ GBM cells are implanted to created a 3-D tumor. Three days later, a portion of the tumor is removed to mimic a resection cavity. Gelfoam® bearing GFP+ NSCs is then seeded into the cavity. (B) The gel was cut into cross sections 1 and 7 days after seeding, and fluorescent imaging was used to visualize the co-localization of the GFP+ NSCs with mCherry+ GBM. We found a large number of NSCs had migrated from the GELFOAM® scaffold, through the agar, and populated the GBM (red) in the day 7 sections. These migratory cells are indicated by arrowheads. These results suggest NSCs are capable of migrating from the GELFOAM®, homing to GBM foci.

DETAILED DESCRIPTION

Figure 1:
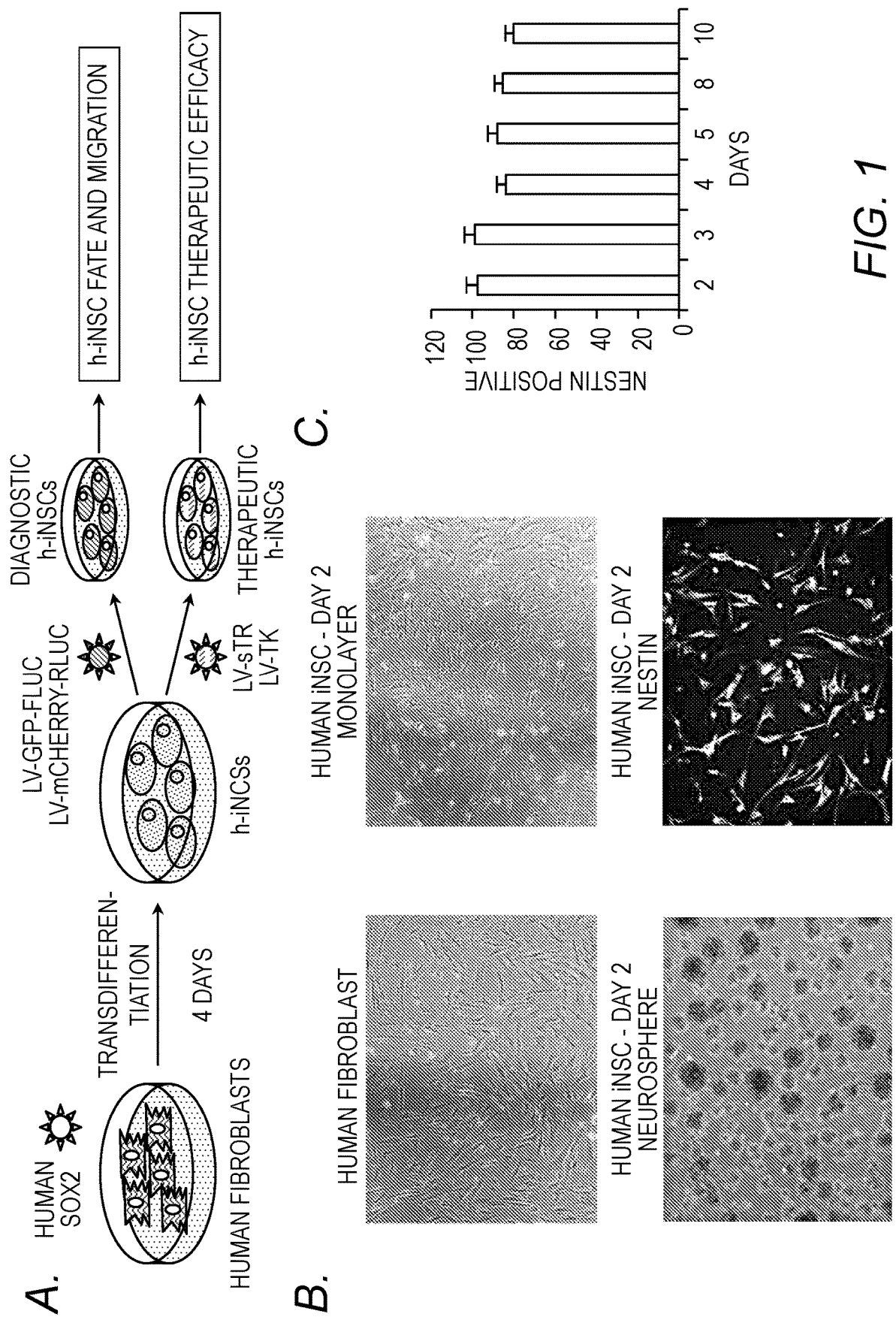
FIG. 1. Generation and characterization of diagnostic and therapeutic INSCs. (A) Schematic depiction of the strategy used to create therapeutic and diagnostic variants of h-iNSCs. Human fibroblasts were transduced with Sox2 and placed in NSC-inducing neural progenitor media. After 4 days, the h-iNSCs were expanded and transduced with optical reporters or tumoricidal transgenes. (B) White light and fluorescent photomicrographs of human fibroblasts and h-iNSCs grown as monolayers, neurospheres, or stained with antibodies against nestin. (C) Summary graph showing the expression of nestin at different days after induction of h-iNSC generation. (D) Immunofluorescent staining that reveals h-iNSC-GFP expression of the NSC marker nestin. GFAP+ astrocytes and Tuj1+ neurons were differentiated from h-iNSC-GFP by mitogen removal. In contrast, no staining was observed for the pluripotency markers TRA-160 or OCT4. Fluorescent images showing only the secondary antibody channel are shown in the bottom row. (E) RT-PCR analysis of Nestin, Sox2, Nanog, and OCT3/4 expression in normal human fibroblasts, h-iNSCs, and h-iPSCs.
Figure 1:
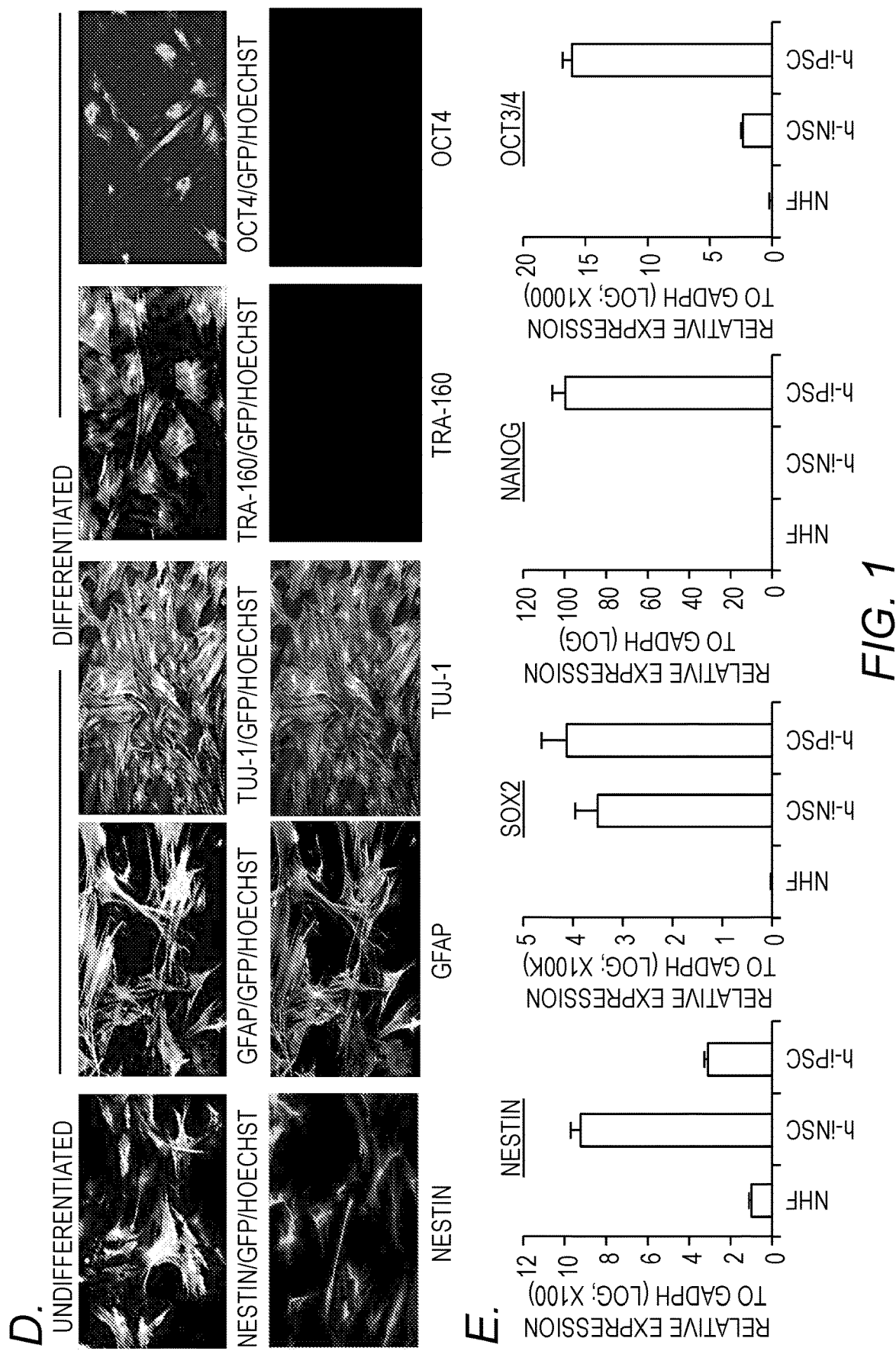

The disclosures of all patent references cited herein are hereby incorporated by reference to the extent they are consistent with the disclosure set forth herein. As used herein in the description of the invention and the appended claims, the singular forms "a," "an" and "the" are intended to include the plural forms as well, unless the context clearly indicates otherwise.

I. Stem Cells

Stem cells useful in the methods of the present invention may be pluripotent or multipotent stem cells, and include, but are not limited to, mesenchymal stem cells and neural stem cells.

A "mesenchymal stem cell" is a pluripotent cell that can differentiate into different cell types, including neuronal cells. See US 2012/0149099 to Molino. Mesenchymal stem cells may be collected as known in the art, e.g., from bone marrow, adipose tissue, or peripheral blood. See U.S. Pat. No. 6,261,549 to Fernandez et al.; PCT publication WO 2014/113704 to Hantash.

A "neural stem cell" as used herein refers to a multipotent cell capable of differentiating into central nervous system cells such as neurons, astrocytes or oligodendrocytes. Neural stem cells may be collected from the central nervous system and/or produced by methods known in the art. See, e.g., U.S. Pat. No. 5,851,832 to Weiss et al., U.S. Pat. No. 8,338,176 to Daadi et al.; U.S. Pat. No. 8,785,187 to Conti et al.; PCT patent application publication WO 2013/124816 to Brodie et al.; WO 2014/035474 to Shah; US 2014/0086907 to Shah; and US 2014/0308256 to Lu et al., which are each incorporated by reference herein. Neural stem cells may also be produced by transdifferentiation as taught herein.

In some embodiments, an induced neural stem cell expresses nestin and/or does not express Nanog or OCT3/4. In some embodiments, an induced neural stem cell is capable of differentiating into a neural/astrocyte cell.

"Transdifferentiation" or "transdifferentiating" is a method in which differentiated somatic cells are directly converted to differentiated or multipotent somatic cells of a different lineage without passing through an intermediate pluripotent stem cell (iPSC) stage. Transdifferentiation may be carried out by exposing the cells to one or more transdifferentation factors and/or growing the cells in a medium that promotes transdifferentiation into the desired cell type. Monitoring the transdifferentiation may be performed using methods known in the art, such as monitoring marker expression indicative of differentiated somatic cells and/or stem cells.

Differentiated somatic cells may be collected from any accessible source, such as tissue, bodily fluids (e.g., blood, urine), etc. In some embodiments, the somatic cell is a fibroblast cell such as a skin fibroblast cell. For example, skin cells may be collected from the boarder of a surgical incision, e.g., during an accompanying surgical procedure, or using a traditional skin punch as a stand-alone procedure. Skin cells can be collected from any area, including, but not limited to, collection from the scalp or forearm.

In some embodiments as taught herein, the transdifferentiating is carried out for a time of from 1, 2, or 3 to 8, 9 or 10 days, from 1, 2 or 4 to 5, 6 or 7 days, from 1 or 2 to 3 or 4 days, or from 12 to 24, 48 or 72 hours.

"Transdifferentiation factor" as used herein is a protein such as a transcription factor that promotes the direct conversion of one somatic cell type to another. Examples include, but are not limited to, Oct4, Sox2, Klf4, Myc, Ascl1, Brn2, Mytl1, Olig2, Zic1, etc. In some embodiments, the method of transdifferentiation is a single-factor transdifferentiation in that only one transdifferentiation factor is used.

"Sox2" is a member of the Sox family of transcription factors and is expressed in developing cells in the neural tube as well as in proliferating progenitor cells of the central nervous system. In some embodiments, Sox2 is used as the transdifferentiation factor in the methods taught. In some embodiments, Sox2 is used to carry out a single-factor transdifferentiation.

"Nestin" is expressed predominantly in stem cells of the central nervous system, and its expression is typically absent from differentiated central nervous cells. "GFAP" or "glial fibrillary acidic protein," is an intermediate filament protein expressed by central nervous system cells, including astrocytes. "Tuj-1" or "βIII tubulin" is a neural marker.

"Nanog" and "OCT3/4" are known stem cell markers.

In some embodiments as taught herein, the transdifferentiating is carried out without the use of feeder cells, e.g., in a neural progenitor medium. Feeder cells, as known in the art, are additional cells grown in the same culture dish or container, often as a layer (e.g., a mouse fibroblast layer on the culture dish) to support cell growth.

"Neural progenitor medium" as used herein is a medium or media that promotes the transdifferentiation (TD) of somatic cells into neural stem cells ("induced" neural stem cells). In some embodiments, the neural progenitor medium includes one or more ingredients selected from: a cell culture medium containing growth-promoting factors and/or a nutrient mixture (e.g., DMEM/F12, MEM/D-valine, neurobasal medium etc., including mixtures thereof); media supplements containing hormones, proteins, vitamins and/or amino acids (e.g., N2 supplement, B27 supplement, non-essential amino acids (NEAA), L-glutamine, Glutamax, BSA, insulin, all trans retinoic acid, etc. including mixtures thereof); and optionally small molecule inhibitors (e.g., SB431542 (BMP inhibitor), LDN193189 (TGF-β1 inhibitor), CHIR99021(GSK3β inhibitor), etc., including mixtures thereof). Ingredients may also include one or more of beta-mercaptoethanol, transferrin; sodium selenite; and cAMP. Suitable concentrations of each of these ingredients are known to those of skill in the art and/or may be empirically determined. Example concentrations of ingredients is also provided in Example 2 below. In some embodiments, the neural progenitor medium is a premade medium, such as STEMdiff™ Neural Induction Medium (STEM-CELL™ Technologies, Vancouver, British Columbia, Canada).

In some embodiments, stem cells are loaded with TERT (telomerase reverse transcriptase) to promote their lifespan and/or enhance their ability to be expanded by cell culture. In some embodiments, the TERT is human telomerase reverse transcriptase ("hTERT").

In some embodiments, stem cells are loaded with (i.e., contain) a therapeutic agent, a reporter molecule, and/or a nucleic acid capable of expressing the same. In some embodiments, the therapeutic agent is a protein toxin (e.g., a bacterial endotoxin or exotoxin), an oncolytic virus (e.g., a conditionally replicative oncolytic adenovirus, reovirus, measles, herpes simplex virus (e.g., HSV1716), Newcatle disease virus, vaccinia, etc.), or a pro-apoptotic agent (e.g., secretable tumor necrosis factor (TNF)-related apoptosis-inducing ligand (S-TRAIL)). See, e.g., WO 2014/018113 to Shah et al.; WO 2009/148488 to Martuza et al.; US 2009/0175826 to Subbiah et al.

In some embodiments, the therapeutic agent is a pro-inflammatory protein such as an interleukin, cytokine, or antibody.

In some embodiments, the therapeutic agent is an enzyme useful for enzyme/prodrug therapies (e.g., thymidine kinase (e.g., with gancyclovir), carboxylesterase (e.g., with CTP-11), cytosine deaminase, etc.).

In some embodiments, the therapeutic agent is an RNAi molecule such as miRNA or siRNA.

In some embodiments, the neural stem cells are loaded with nanoparticle/drug conjugates.

Reporter molecules are known in the art and include, but are not limited to, green fluorescent protein, β-galactosidase, alkaline phosphatase, luciferase, and chloramphenicol acetyltransferase gene. See, e.g., US 2013/0263296 to Pomper et al.

Loading of the stem cells may be accomplished using art-known methods, such as transfecting the cells with a nucleic acid capable of producing a therapeutic or reporter protein, transducing the cells with a viral vector, lipid-based or polymeric loading of the cells with a therapeutic agent and/or reporter molecule, etc.

"Transfecting" is the transfer of heterologous genetic material into a cell, often through the use of a vector (i.e., molecule used as a vehicle to carry foreign genetic material into another cell). Methods of transfecting eukaryotic cells are known, and may include, but are not limited to, electroporation, use of cationic liposome based reagent, nanoparticle polymer liposomes, etc.

"Transducing" is the transfer of heterologous genetic material into a cell by means of a virus. Such viral vectors are known and may include, but are not limited to, lentiviral vectors, adenoviral vectors, etc.

In some embodiments, the nucleic acid capable of producing a therapeutic agent and the nucleic acid encoding the transdifferentiation factor are provided on the same vector.

II. Delivery Vehicles and Methods of Use

As used herein, a "delivery vehicle" or "scaffold" is a substrate in which stem cells as taught herein may be loaded or incorporated for delivery in a method of treatment as taught herein.

In contrast to many regenerative medicine applications in which scaffolds become part of the structure of an organized tissue, scaffolds of the present invention should allow the stem cells to migrate away from the scaffold and towards the cancer or damaged tissue, with sufficient numbers and viability to minimize toxicity from damaged cells and enable their effectiveness at the site of action, particularly in the delicate central nervous system.

For example, in some regenerative medicine applications, cells must persist for the life of the patient, remain at the site of transplant to regenerate the damaged area, typically are not engineered to release agents, and/or rely on appropriate differentiation cues to form a target tissue. By contrast, in drug delivery applications, cell persistence can be matched to tumor eradication, cells must efficiently migrate off of scaffolds to track invasive cancer foci, cells may release cytotoxic agents to kill tumors, and/or differentiation into non-migratory cell types is not desired.

"Treat" or "treatment" as used herein refers to any type of treatment that imparts a benefit to a patient afflicted with a disease or disorder such as a cancer, neurodegenerative disorder or neural trauma, including improvement in the condition of the patient (e.g., in one or more symptoms), delay in the progression of the disease, delay in onset or recurrence of the disease, etc.

The present invention is primarily concerned with the treatment of human subjects, but the invention may also be carried out on animal subjects, particularly mammalian subjects such as mice, rats, dogs, cats, livestock and horses for veterinary purposes, and for drug screening and/or drug development purposes. Subjects may be of any age, including infant, juvenile, adolescent, adult, and geriatric subjects.

In some embodiments, stem cells are allogeneic or autologous with respect to the subject.

Cancers to be treated include brain cancers, which may be primary or secondary brain cancer. A "primary brain cancer" is an intracranial cancer of central nervous system cells. Types of such brain cancer includes gliomas (e.g., glioblastoma or glioblastoma multiforme (GBM)), meningiomas, medulloblastomas, pituitary adenomas and nerve sheath tumors. A "secondary brain cancer" is a cancer located in the central nervous system that includes cells metastasized from other areas of the body, e.g., breast cancer, melanoma, lung cancer, prostate cancer, etc.

Administration of the delivery vehicle or scaffold may be performed using methods known in the art. For example, intracranial administration of the may be performed for the treatment of a brain cancer, preferably intratumoral administration or intracavity administration performed after surgical removal of at least a part of a brain tumor.

In some embodiments, the stem cells are autologous with respect to the subject to be treated, and administering is carried out 1, 2, 3 or 4, to 7, 10, 14 or 21 days, after transdifferentiating an autologous somatic cell.

In some embodiments, the cells are encapsulated by a matrix such as a hydrogel matrix (e.g., a synthetic extracellular matrix), and/or seeded onto a scaffold, which may then be administered or implanted, e.g., intracranially. See, e.g., PCT patent application publication WO 2014/035474 to Shah; US 2014/0086907 to Shah, which are each incorporated by reference herein.

In some embodiments, the scaffold is "pliable" to allow manipulation thereof prior to or during administration to conform the scaffold to the area to which the cell cargo is being delivered, such as the walls of a tumor resection cavity. "Pliable" means that the scaffold is easily bendable and/or malleable without loss of the scaffold's structural integrity. A pliable scaffold may also allow reshaping of the scaffold after administration.

In some embodiments, the average thickness of the scaffold is in the nanometer, micrometer or millimeter range. In some embodiments, the scaffold is configured to line the walls of the resection cavity. In some embodiments, the scaffold has ridges, channels and/or aligned fibers to promote movement of the stem cells in the direction of the cancer or damaged tissue.

Preferably, the delivery vehicles are biocompatible, and in some embodiment the delivery vehicles are biodegradable and/or bioabsorbable. As used herein, "biocompatible" refers to materials that are not unduly reactive or harmful to a subject upon administration. "Biodegradable" as used herein refers to the ability of a material to be broken down in vivo upon administration to a subject. "Bioabsorbable" as used herein means capable of being absorbed into living tissue. Example bioabsorbable materials include, but are not limited to, bioabsorbable polymers such as polyanionic polysaccharides (e.g., hyaluronic acid (HA), carboxymethylcellulose (CMC), carboxymethylamylose (CMA), chondroitin-6-sulfate, dermatin sulfate, dermatin-6sulfate and combinations thereof), alginic acid, chitin, chitosan, fibrin, dextran, polylactic acid, polyglycolic acid, poly(D−)lactic acid, polyglycoliclactic acid, keratin, laminin, elastin, collagen and other naturally-occurring extracellular matrix proteins, gelatin, polydioxanones, polycaprolactone, and blends and co-polymers thereof. See, e.g., US 2009/0105671 to Dagger et al.; U.S. Pat. No. 8,048,446 to Lelkes et al.

In some embodiments, the delivery vehicle includes an electrospun scaffold. The materials may be electrospun by methods known to those skilled in the art. For example, they may be solvent spun using appropriate solvents, such as dimethylformamide, methylene chloride, chloroform, dichloromethane, acetonitrile, methanol, N-methylpyrrolidone, hexafluoroisopropanol and dimethyl sulphoxide, with appropriate additives, such as sodium chloride, magnesium chloride, potassium dihydrogen phosphate, potassium iodate, potassium phosphate, calcium carbonate, calcium phosphate and calcium lactate, in solution form or in nanoparticulate forms, and any other additives, solvents, polymers, bioactives, pharmaceutical agents, metals, metal oxides or cells or cellular components known to one skilled in the art, that can be integrated into an electrospun format.

The delivery vehicle may also include a matrix of a wet-electrodeposited biodegradable, elastomeric polymer, such as poly(ester urethane) urea (PEUU), poly(ether ester urethane)urea (PEEUU), poly(ester carbonate)urethane urea (PECUU) and poly(carbonate)urethane urea (PCUU). See US 2014/0377213 to Hong et al.

In some embodiments, the cells are provided in a fibrin glue. Fibrin glues are known, and formed upon mixing of fibrinogen and thrombin. See, e.g., U.S. Pat. No. 6,056,970 to Greenawalt et al.; U.S. Pat. No. 6,699,484 to Whitmore et al.; US 2011/0296542 to Wang et al.

In some embodiments, the cells are mixed with the fibrinogen and thrombin upon administration, e.g., to the surgical wall after surgical removal of at least a part of a brain tumor.

Fibrin is a natural biopolymer that forms a scaffold to promote cell attachment during wound healing. See Weisel, Fibrinogen and fibrin. *Advances in protein chemistry* 70, 247-299 (2005). Unlike slowly-forming extracellular matrices, fibrin scaffolds rapidly assemble upon the combination of fibrinogen and thrombin into three-dimensional branching fibers, following the cleavage of fibrinogen polypeptides by activated thrombin.

In some embodiments, a rapidly polymerizing matrix is preferred to both shorten surgical time and eliminate the risk of physical washout of stem cells from the surgical cavity during scaffold gelation. In some embodiments, the gelation time is less than 20, 15, 10, 5, 2 or 1 minutes.

In preferred embodiments, the matrix material is biocompatible to avoid immune reaction and biostable to provide lasting structural support for the therapeutic stem cells in the cavity. The material should support retention of stem cells within the surgical cavity, and allow therapeutic agents released from cytotoxic stem cells to penetrate the matrix and induce killing in the cancerous cells. The matrix material should also not unduly slow the migration of stem cells out of the matrix and towards cancerous cells.

In some embodiments, the delivery vehicle is a bioabsorbable fibrin material (e.g., TISSEEL® fibrin sealant). Fibrin has a low mechanical stiffness allowing it to easily conform to structures. See Janmey et al., The hard life of soft cells. *Cell Motil Cytoskeleton* 66, 597-605 (2009). It also has a rapid gelation time, making it capable of trapping cells in the matrix within seconds and before they can be washed out or lost from the vertical face of the resection cavity walls. See Rowe et al., Influence of thrombin concentration on the mechanical and morphological properties of cell-seeded fibrin hydrogels. *Acta Biomater* 3, 59-67 (2007). Fibrin is also able to be heavily loaded with cells without affecting polymerization. As a protein matrix, fibrin gel is broken down by the body's natural clearance mechanisms and creates non-toxic breakdown products. The hemostatic function of the fibrin scaffold may also aid in controlling any post-surgical bleeding in the surgical resection cavity.

In some embodiments, the delivery vehicle is a bioabsorbable crosslinked gelatin sponge material (e.g., GELFOAM® absorbable gelatin compressed sponge). Gelatin sponges may be made by foaming a solution of gelatin and drying the foam, usually by lyophilization. The gelatin of the sponge is crosslinked in order to maintain its structural integrity in vivo. Methods of crosslinking may include treatment of the sponge with a chemical crosslinking agent such as, e.g., formaldehyde, glutaraldehyde, carbadiimides (e.g., EDC) and/or heat treatment of the dry sponge with dry heat (e.g., 100-160° C. for several hours). See, e.g., U.S. Pat. No. 5,512,301 to Song et al.; U.S. Pat. No. 8,475,812 to Nur et al.

Preferably, the delivery vehicle maintains the viability and/or proliferative capacity of the cells in the area of treatment ("persistence"), though allowing cell migration away from the scaffold, for at least 5 days, at least 8 days, at least 10 days, at least 12 days, at least 15 days, at least 18 days, at least 20 days, at least 25 days, at least 30 days, at least 35 days, at least 40 days, at least 45 days, or longer, though the delivery vehicle may be biodegradable and/or bioabsorbable.

The present invention is explained in greater detail in the following non-limiting examples.

EXAMPLES

Example 1: Rapid Transdifferentiation of Human Skin Cells

The ability to rapidly generate human induced neural stem cells (h-iNSCs) from human skin may enable patient-specific therapies to treat cancer. The efficiency of iNSC generation is significantly higher than other cellular reprogramming strategies, suggesting large numbers of h-iNSCs could be generated from small amounts of skin. Patient-specific derivation could avoid immune rejection to maximize tumor killing and for treatment durability.

Cell-based drug carriers must be generated quickly in order to treat patients with rapidly progressing cancers, and h-iNSCs can be created in weeks. Also, unlike iPSCs, h-iNSCs do not form teratomas after transplant.

In this study, the potential of transdifferentiation-derived h-iNSC therapies was investigated as autologous GBM therapy for human patients. These methods are capable of converting human skin into h-iNSCs 6-fold faster than previous methods, which is significant because time is a priority for GBM patient therapy. This strategy was used to create the first h-iNSCs engineered with cytotoxic agents and optical reporters. A combination of real-time molecular imaging, 3-D cell culture, and multiple human GBM xenografts models were used to investigate the fate, tumor-specific homing, and efficacy of h-iNSC therapy against solid and surgically resected GBM.

Materials and Methods

Cell Lines:

U87, GBM8, GBM4, 293T, and human fibroblast cells (CCD-1099Sk, others) were grown as previously described (Hingtgen et al., Stem Cells 28, 832-841, 2010; Wakimoto et al., Cancer Res 69, 3472-3481, 2009). Lentiviral vectors (LV) encoding hTERT and Sox2 were purchased from Addgene (Cambridge. Mass., USA). All cDNA were under control of the tetracycline promoter.

Human iNSCs (h-iNSC) were generated following a single-factor Sox2 and feeder-free method. Briefly, 200,000 human fibroblasts were seeded in 6-well plates and transduced with the LV cocktail containing hTERT and Sox2 in media containing protamine sulfate (5 µg/ml, Sigma). Two days after infection, the media was changed to STEMdiff™ Neural Induction Medium (STEMCELL Technologies, Vancouver, Canada) containing doxycycline (10 µg/ml, Sigma, St. Louis, Mo., USA). Media was changed every 3 days. Neurosphere formation was induced by culturing in low-adherent flasks.

Lentiviral Vectors:

In addition to the reprogramming vectors, the following lentiviral vectors were used in this study: LV-GFP-FL, LV-GFP-RLuc, LV-mC-FL, LV-sTR, LV-diTR and LV-mRFP-hRLuc-ttk. GFP-RLuc and GFP-FL were constructed by amplifying the cDNA encoding *Renilla* luciferase or firefly luciferase using the vectors luciferase-pcDNA3 and pAC-hRluc (Addgene), respectively. The restriction sites were incorporated in the primers, the resulting fragment was digested BglII and SalI, and ligated in frame in BglII/SalI digested pEGFP-C1 (Clontech, Mountain View, Calif., USA). The GFP-FL or GFP-RLuc fragments were digested with AgeI (blunted) and SalI, and ligated into pTK402 (provided by Dr. Tal Kafri, UNC Gene Therapy Center) digested BamHI (blunted) and XhoI to create LV-GFPFL or LV-GFP-RLuc. Similarly, mCFL was created by amplifying the cDNA encoding firefly luciferase from luciferase-pcDNA3, ligating into BglII/SalI digested mCherry-C1 (Clontech), and ligating the mC-FL fragment into pTK402 LV backbone using blunt/XhoI sites. To create LV-sTR and LV-diTR, the cDNA sequence encoding sTR or diTR was PCR amplified using custom-synthesized oligonucleotide templates (Invitrogen, Carlsbad, Calif., USA). The restriction sites were incorporated into the primers, the resulting fragment was digested with BamH1 and XhoI, and ligated in-frame into BamH1/XhoI digested pLVX plasmid. Both LV-sTR and LV-diTR have IRES-GFP (internal ribosomal entry sites-green fluorescent protein) elements in the backbone as well as CMV-driven puromycin element. All LV constructs were packaged as LV vectors in 293T cells using a helper virus-free packaging system as described previously (Sena-Esteves et al., Journal of virological methods 122, 131-139, 2004). h-iNSCs and GBM cells were transduced with LVs at varying multiplicity of infection (MOI) by incubating virions in a culture medium containing 5 µg/ml protamine sulfate (Sigma) and cells were visualized for fluorescent protein expression by fluorescence microscopy.

Cell Viability and Passage Number:

To assess the proliferation and passage number of modified and unmodified h-iNSCs, h-iNSCs expressing GFP-FL, sTR or unmodified cells were seeded in 96-well plates. Cell viability was assessed 2, 3, 4, 5, 8, and 10 days after seeding using CellTiter-Glo® luminescent cell viability kit (Promega). Maximum passage number was assessed by monitoring the number of times INSCs, iNSC-sTR, or WT-NSC were subcultured without alterations in morphology, growth rate, or transduction efficiency.

Immunohistochemistry and In Vitro Differentiation:

To determine the effects of LV modification on h-iNSC differentiation, h-iNSCs were transduced with LV-GFP-FL or LV-sTR. Engineered or unmodified cells were fixed, permeabilized, and incubated for 1 h with anti-nestin Polyclonal antibody (Millipore, MAB353, 1:500, Billerica, Mass., USA). Cells were washed and incubated with the appropriate secondary antibody (Biotium, Hayward, Calif., USA) for 1 hr. Cells were then washed, mounted, and imaged using fluorescence confocal microscopy. For differentiation, engineered or non-transduced h-iNSCs were cultured for 12 days in N3 media depleted of doxycycline, EGF, and FGF. Cells were then stained with antibodies directed against nestin, glial fibrillary acidic protein (GFAP; Millipore, MAB3405, 1:250), or Tuj-1 (Sigma, T8578, 1:1000) and detected with the appropriate secondary antibody (Biotium). Nuclei were counterstained with Hoechst 33342 and the results analyzed using a FV 1200 laser confocal microscope (Olympus, Center Valley, Pa.).

Three-Dimensional Tissue Culture.

Three-dimensional levitation cell cultures were performed using the Bio-Assembler Kit (Nano3D Biosciences, Houston, Tex.). Confluent 6 well plates with GBM or h-iNSC were treated with a magnetic nanoparticle assembly (8 μl cm$^{-2}$ of cell culture surface area or 50 μl ml$^{-1}$ medium, NanoShuttle (NS), Nano3D Biosciences) for overnight incubation to allow for cell binding to the nanoparticles. NS was fabricated by mixing iron oxide and gold nanoparticles cross-linked with poly-1-lysine to promote cellular uptake. (Souza, G. R., et al. Three-dimensional tissue culture based on magnetic cell levitation. Nat Nanotechnol 5, 291, 2010). Treated GBM and h-iNSC were then detached with trypsin, resuspended and mixed at different ratios (1:1 and 1:0.5) in an ultra-low attachment 6 well plate with 2 ml of medium. A magnetic driver of 6 neodymium magnets with field strength of 50 G designed for 6-well plates and a plastic lid insert were placed atop the well plate to levitate the cells to the air-liquid interface. Media containing 4 μg/ml GCV was added to the co-culture of GBM with h-iNSC expressing ttk. Fluorescence images where taken over time to track the cell viability of both populations (previously labeled with different fluorescence). For BLI of 3D cell culture, 100 dl/well of Fluc substrate stock reagent was added to the media and imaged using an IVIS Kinetic Optical System (PerkinElmer) with a 5 minute acquisition time. Images were processed and photon emission quantified using LivingImage software (PerkinElmer).

Real-Time Imaging and Motion Analysis:

Migration was assessed in novel 2-dimensional and 3-dimensional culture systems.

2-Dimensional Migration:

h-iNSCs expressing RFP were seeded in micro-culture inserts in glass bottom microwell dishes (MatTek, Ashland, Mass., USA) using 2-chamber cell culture inserts (ibidi, Verona, Wis., USA). U87 glioma cells expressing GFP were plated into the adjacent well (0.5 mm separation) or the well was left empty. 24 hrs after plating, cells were placed in a VivaView live cell imaging system (Olympus) and allowed to equilibrate. The insert was removed and cells were imaged at 10× magnification every 20 minutes for 36 hours in 6 locations per well (to monitor sufficient cell numbers) in three independent experiments. NIH Image was then used to generate movies and determine both the migrational velocity, total distance migrated, and the directionality of migration.

3-Dimensional Migration:

h-iNSC migration to GBM spheroids was assessed in 3-D culture systems by creating h-iNSC and GBM spheroids using levitation culture as described above. h-iNSC and GBM spheroids were co-cultured in levitation systems. Real-time imaging was performed to visualize the penetration of GBM spheroids by h-iNSCs in suspension.

Co-Culture Viability Assays:

mNSC expressing sTR or control GFP-RL (5×10$^3$) were seeded in 96 well plates. 24 hrs later, U87-mC-FL, LN18-mC-FL, or GBM8-mC-FL human GBM cells (5×10$^3$) were seeded into the wells and GBM cell viability was measured 24 hrs later by quantitative in vitro bioluminescence imaging. GBM cells were also assessed at 18 hrs for caspase-3/7 activity with a caged, caspase 3/7-activatable DEVD-aminoluciferin (Caspase-Glo 3/7, Promega, Madison, Wis., USA).

h-iNSC Survival and Fate In Vivo:

To determine the survival of h-iNSCs in vivo, h-iNSC expressing mCherry-FL (7.5×10$^6$ cells/mouse) were suspended in PBS and implanted stereotaxically into the right frontal lobe of mice (n=7). h-iNSC survival was determined by serial bioluminescence imaging performed for 20 days. To determine the fate of h-iNSCs at a cellular resolution, animals were sacrificed 21 days post-implantation, brains extracted sectioned. Tissue sections were stained with antibodies against nestin, GFAP, Tuj-1, Oct-4, and TRA-160, and visualized using a secondary antibody labeled with CF™ 488.

Co-Culture Viability Assays:

3-D levitation culture was used in three separate in vitro cytotoxicity studies. h-iNSCs expressing 2 different cytotoxic agents were used to treat 1 established GBM cell line (U87) and 2 patient-derived GBM lines (GBM4, GBM8). 1) To determine the cytotoxicty of TRAIL therapy, h-iNSC-sTR or h-iNSC-mCherry spheroids were co-cultured in suspension with U87-GFP-FLuc spheroids at a iNSC:GBM ratio of 1:2 or 1:1. GBM spheroid viability was determined 48 hrs later by FLuc imaging. 2) To determine the cytotoxicity of pro-drug enzyme therapy for patient-derived GBMs, h-iNSC-TK spheroids were co-cultured in suspension with patient-derived GBM4-GFP-FLuc spheroids or mixed with GBM cells prior to sphere formation. Spheroids were cultured with or without gancyclovir (GCV) and GBM spheroid viability was determine 0, 2, 4, or 7 days after addition of the pro-drug by FLuc imaging. 3) To determine the cytotoxicity of sECM-encapsulated INSC pro-drug/enzyme therapy, h-iNSC-TK were encapsulated in sECM and placed in levitation cultured with patient-derived GBM8-GFP-FLuc spheroids. Viability was determine by FLuc imaging.

Anti-GBM Efficacy of h-iNSC Therapy In Vivo: Three different xenograft studies were performed to assess the anti-GBM effects of h-iNSC therapy. h-iNSC-sTR and h-iNSC-TK therapy was tested against solid (U87), diffused patient-derived (GBM8), and surgically resected patient-derived (GBM4) xenograft models.

1) To determine the therapeutic efficacy of h-iNSC-TRAIL against solid human U87 tumors, a combination of h-iNSC-TRAIL or iNSC-GFP-RLuc (7.5×10$^5$ cells/mouse) were stereotactically implanted into the right frontal lobe of mice (n=7) together with U87-mC-FL cells (1×10$^6$ cells/mouse). Therapeutic response was then determined by following tumor volumes with FL bioluminescence imaging as described previously. Briefly, mice were given an intraperitoneal injection of D-Luciferin (4.5 mg/mouse in 150 dl of saline) and photon emission was determined 5 minutes later using an IVIS Kinetic Optical System (PerkinElmer) with a 5 minute acquisition time. Images were processed and photon emission quantified using LivingImage software (PerkinElmer). Additionally, mice were followed for survival over time.

2) To investigate the efficacy of h-iNSC prodrug/enzyme therapy against invasive patient-derived GBM, mice were stereotactically implanted in the right frontal lobe with GBM8 cells expressing mC-FL (1.5×10$^5$ cells/mouse). Three days later, h-iNSC-TK (n=7, 7.5×10$^5$ cells/mouse) or h-iNSC-mRFP-hRLuc (n=7, 7.5×10$^5$ cells/mouse) were implanted into the tumor implantation site. GCV was injected i.p. daily during two weeks at a dose of 100 mg/kg.

Changes in tumor volume were assessed by FLuc imaging as described above and mice were followed for survival over time.

3) To determine the efficacy of h-iNSC therapy against post-surgical minimal GBM, image-guided GBM resection in mice was performed according to our previously reported strategy. Patient-derived GBM8-GFP-FLuc were harvested at 80% confluency and implanted stereotactically ($5 \times 10^5$ cells) in the right frontal lobe: 2 mm lateral to the bregma and 0.5 mm from the dura. Following immobilization on a stereotactic frame, mice were placed under an Olympus MVX-10 microscope. Intraoperative microscopic white light, GFP, and RFP images were captured throughout the procedure using with a Hamamatsu ORCA 03G CCD (high resolution) camera and software (Olympus). A midline incision was made in the skin above the skull exposing the cranium of the mouse. The intracranial xenograft was identified using GFP fluorescence. A small portion of the skull covering the tumor was surgically removed using a bone drill and forceps and the overlying dura was gently peeled back from the cortical surface to expose the tumor. Under GFP fluorescence, the GBM8-GFPFL tumor was surgically excised using a combination of surgical dissection and aspiration, and images of GFP were continuously captured to assess accuracy of GFP-guided surgical resection. Following tumor removal, the resulting resection cavity was copiously irrigated and the skin closed with 7-0 Vicryl suture. No procedure-related mortality was observed. All experimental protocols were approved by the Animal Care and Use Committees at The University of North Carolina at Chapel Hill and care of the mice was in accordance with the standards set forth by the National Institutes of Health *Guide for the Care and Use of Laboratory Animals*, USDA regulations, and the American Veterinary Medical Association. Following surgical resection, h-iNSC-TK or h-iNSC-mC-FL ($5 \times 10^5$ cells) were encapsulated in hyaluronic sECM hydrogels (Sigma) and transplanted into the post-operative GBM cavity. GBM recurrence was visualized by FLuc imaging as described above and mice were followed for survival.

Tissue Processing:

Immediately after the last imaging session, mice were sacrificed, perfused with formalin, and brains extracted. The tissue was immediately immersed in formalin. 30 µm coronal sections were generated using a vibrating microtome (Fisher Waltham, Mass., USA). For nestin, GFAP, and Tuj-1 staining, sections were incubated for 1 hr in a blocking solution (0.3% BSA, 8% goat serum, and 0.3% Triton X-100) at room temperature, followed by incubation at 4° C. overnight with the following primary antibodies diluted in blocking solution: (1) anti-human nestin (Millipore), (2) anti GFAP (Millipore), (3) anti TRAIL (ProSci, Poway, Calif.) and (4) anti-Tuj-1 (Sigma). Sections were washed three times with PBS, incubated in the appropriate secondary antibody, and visualized using a confocal microscope (Olympus).

Results

The Rapid Transdiferentiation of Human Fibroblasts into h-iNSCs.

The rapid and efficient generation of h-iNSC therapies is essential for treating patients with aggressive cancer. As a new strategy, human fibroblasts were transduced with Sox2 and performed h-iNSC generation without feeder cells. Then diagnostic h-iNSCs expressing optical reporters or therapeutic h-iNSCs expressing different cytotoxic agents were generated (FIG. 1A). First was evaluated the kinetics of generating h-iNSCs using the feeder-free/Sox2 strategy. Human fibroblasts were transduced with Sox2 and cultured in NSC-inducing media (FIG. 1B). Changes in cell morphology were observed within 48 hrs of activating Sox2 expression. Additionally, wide-spread nestin expression was detected and the h-iNSCs could form neurosphere formation. Quantification showed nestin expression in h-iNSCs remained constant from day 2 through day 10 (FIG. 1C). When induced to differentiate, the h-iNSCs expressed the astrocyte marker GFAP and the neural marker Tuj-1. Staining revealed the cells did not express the pluripotency makers TRA-160 or OCT4 (FIG. 1D). These findings were confirmed by RT-PCR analysis (FIG. 1E). The h-iNSCs showed high level of nestin expression that was absent in parental fibroblasts or human iPSC (h-iPSC). Sox2 expression was high in both h-iNSCs and h-iPSCs because Sox2 overexpression was used to generate both cell lines. Unlike h-iPSCs, h-iNSCs did not express high levels of the pluripotency markers Nanog or OCT3/4. Together, these data demonstrate the ability to create multi-potent h-iNSCs within 48 hrs using single-factor Sox2 expression.

h-iNSCs Migrate Selectively to GBM.

Figure 2:
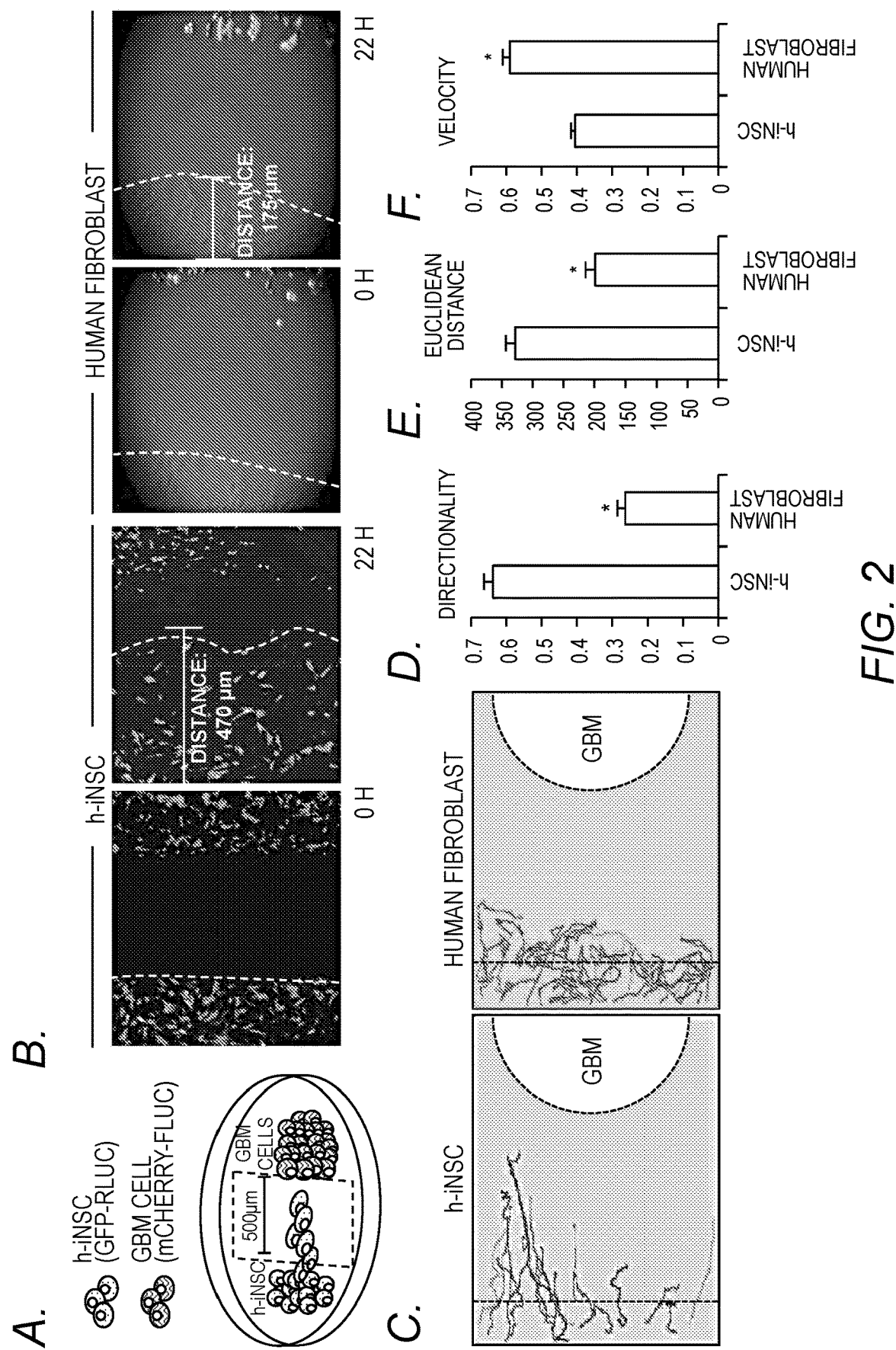
FIG. 2. Engineered h-iNSCs home to GBM. (A) h-iNSC-GFPFL were seeded 500 µm apart from mCherry-expressing human GBM cells and placed in a fluorescence incubator microscope. Time-lapse fluorescent images were captured every 10 minutes for 24 hours and used to construct movies that revealed the migration of iNSC in real-time. (B) Summary images showing migration of h-iNSC-GFPFL or parental human fibroblasts towards U87-mCFL at 0 hrs and 24 hrs after plating. (C) Single cell tracings depicting the path of h-iNSC-GFPFL directed migration towards GBM over 24 hrs. Additional images show the limited migration of parental human fibroblasts. Dotted line indicates the site of GBM seeding. (D-F) Summary graph showing the directionality (D), distance (E), and velocity (F) of h-iNSCs or fibroblast migration towards GBM cells determined from the real-time motion analysis. (G-H) To assess h-iNSC migration to solid GBMs, U87 GBM spheroids were co-cultured with h-iNSCs in a 3D leviation system (G) Fluorescent imaging showed the migration of h-iNSC-GFPFL into U87 spheroids and their penetration towards the core of the tumor spheroid over time (H).
Figure 2:
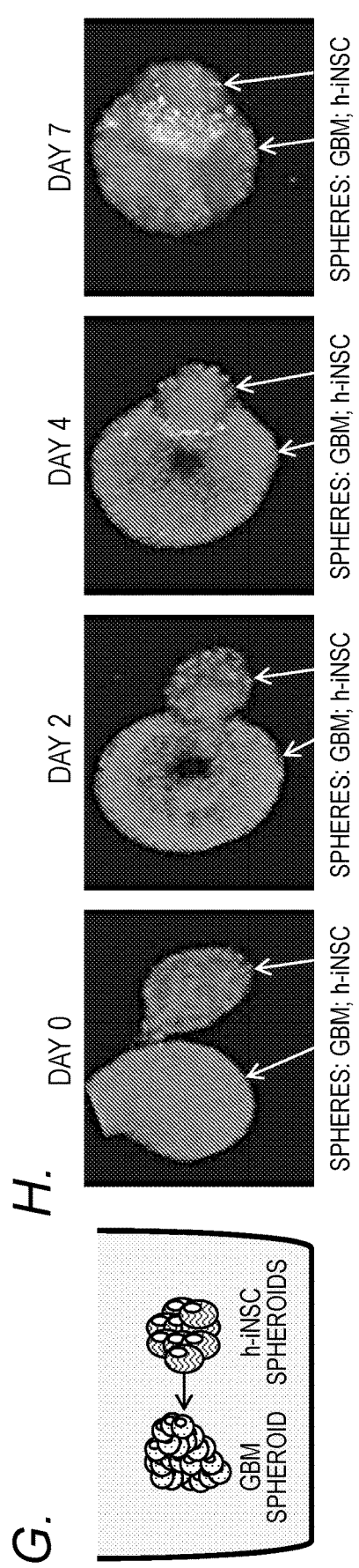

The ability to home to solid and invasive GBM deposits is one of the most beneficial characteristics of NSC-based cancer therapies. To investigate the tumor-tropic nature of h-iNSCs, we used real-time motion analysis of h-iNSCs co-cultured with human GBM cells (outlined in FIG. 2A). For reference, h-iNSC migration was compared to the parental human fibroblasts from which they were derived. It was found that h-iNSCs rapidly migrated towards the co-cultured GBM cells, covering the 500 m gap in 22 hrs (FIG. 2B). Single cell migratory path analysis showed that the presence of GBM cells induced h-iNSC to selectively migrate towards the co-cultured GBM cells (FIG. 2C). In contrast, human fibroblasts demonstrated very little migration (FIG. 2B). Single cell migration analysis of human fibroblasts confirmed the random migratory patterns with very little displacement towards the co-cultured GBM cells (FIG. 2C). The directionality of the migration of h-iNSC was analyzed by calculating the ratio of Euclidian distance to overall accumulated distance, with perfect single direction movement yielding a ratio of 1.0 and perfectly non-directional movement yielding a ratio of 0.0. Using this analysis, we calculated an average directionality ratio that was significantly higher for h-iNSCs (0.65) than human fibroblasts (0.28) (FIG. 2D). Further analysis of single cell migration patterns demonstrated significantly increased average Euclidian distance migrated by h-iNSC (340 µm) as compared to human fibroblasts (200 µm) (FIG. 2E). The average cell velocity by h-iNSC was lower as compared to human fibroblasts (0.4 vs 0.62) (FIG. 2F). Lastly, we performed 3-D migration assays to mimic the in vivo migration of h-iNSCs into GBM foci. mCherry+h-iNSC spheroids were co-cultured with GFP+ GBM spheroids and both cell types were levitated using magnetic force (FIG. 2G). We discovered that the h-iNSCs began penetrating the GBM spheroids within hours of seeding. The h-iNSC spheroids continued to penetrate the GBM spheroids, extensively co-localizing within 8 days. Together, these observations support the conclusion that h-iNSCs possess tumoritropic properties and home to GBM cells.

h-iNSC Persistence and In Vivo Fate.

Figure 3:
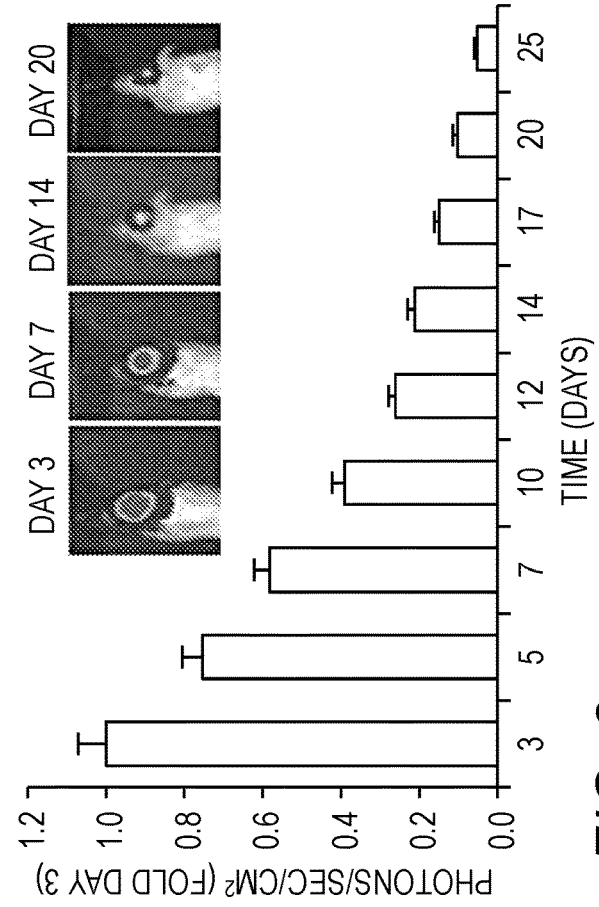
FIG. 3. In vivo characterization of INSCs transplanted in the mouse brain. (A) summary graph demonstrating the proliferation of unmodified h-iNSCs and h-iNSCs engineered to express mCherry-FLuc. (B-C) h-iNSC were implanted into the frontal lobe of mice and serial bioluminescence imaging was used to monitor their persistence over 3 weeks. Summary graphs demonstrated the h-iNSCs persisted in the brain from 25 days, although they were gradually cleared (B). Immunofluorescence analysis of h-iNSCs 14 days post-implantation into the brain showed Nestin+ and Tuj+ cells, however no co-localization between h-iNSCs and the pluripotency markers Oct-4 and TRA-160 was observed (C).
Figure 3:
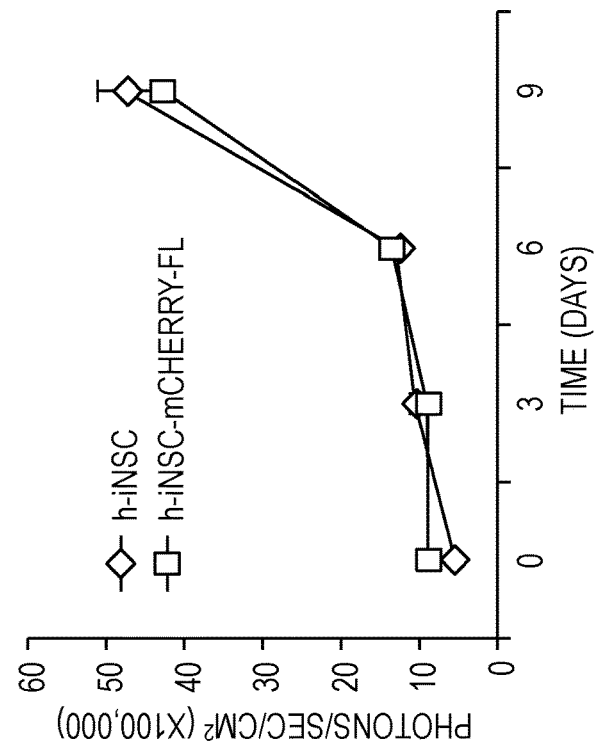
Figure 3:
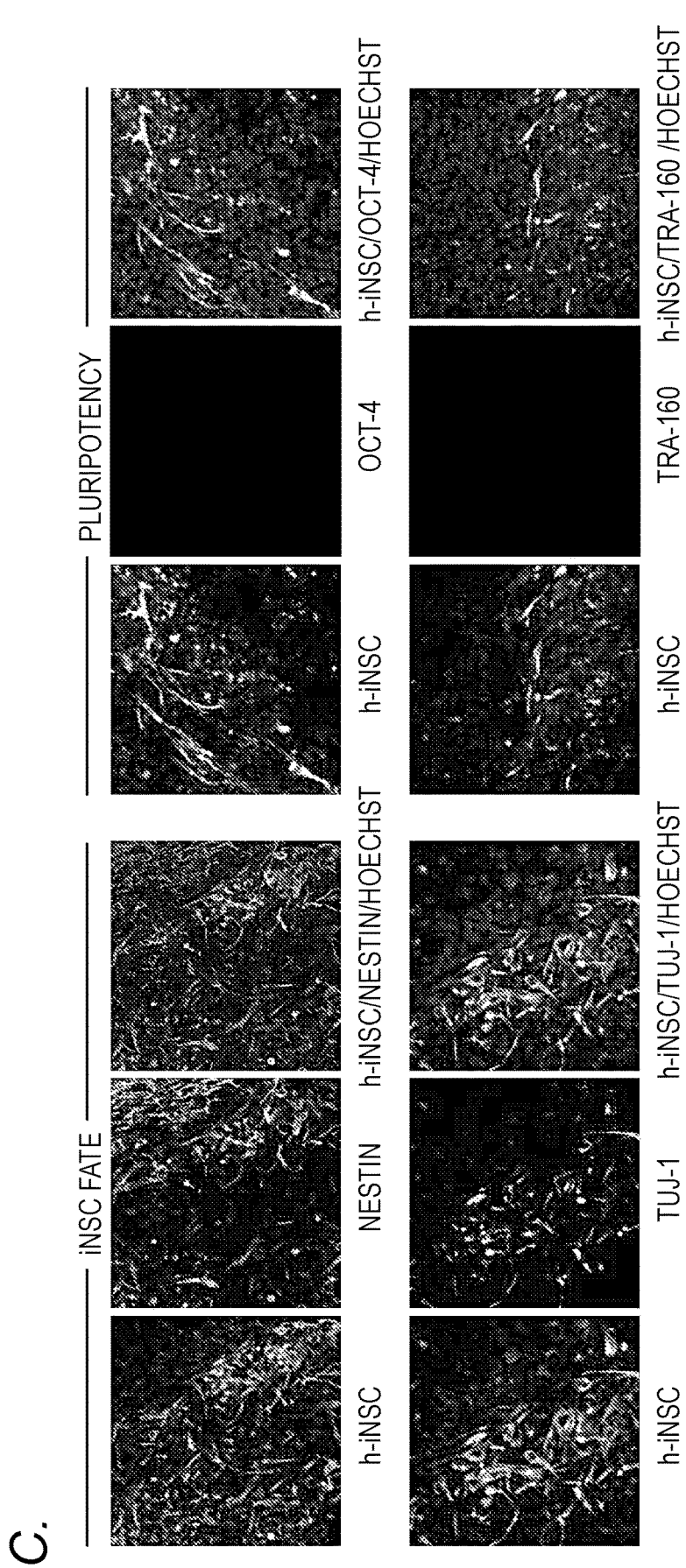

We next utilized the engineered h-iNSCs to investigate the survival and fate of these cells in vivo in the brain. A previous study of in vitro proliferation after engineering of h-iNSC with GFPFL and mCFL showed no significant differences with non-engineered h-iNSCs (FIG. 3A). For in vivo study, h-iNSCs engineered with mCFL was stereotactically implanted in the brain of mice and real-time noninvasive imaging was used to monitor cell survival over time. Capturing images periodically, we found that h-iNSCs survive more than 20 days post implantation (FIG. 3B). Post-mortem IHC revealed that approximately half of h-iNSC-mCFL expressed the NSC marker nestin (FIG. 3D) and the other half were positive for the neuronal marker Tuj-1 (FIG. 3D). No astrocyte marker GFAP was observed. Additional IHC verified the transplanted h-iNSCs did not express the pluripotency markers Oct-4 and TDR-160.

Efficacious Treatment of Malignant and Invasive GBM Using Tumoricidal iNSCs.

Figure 4:
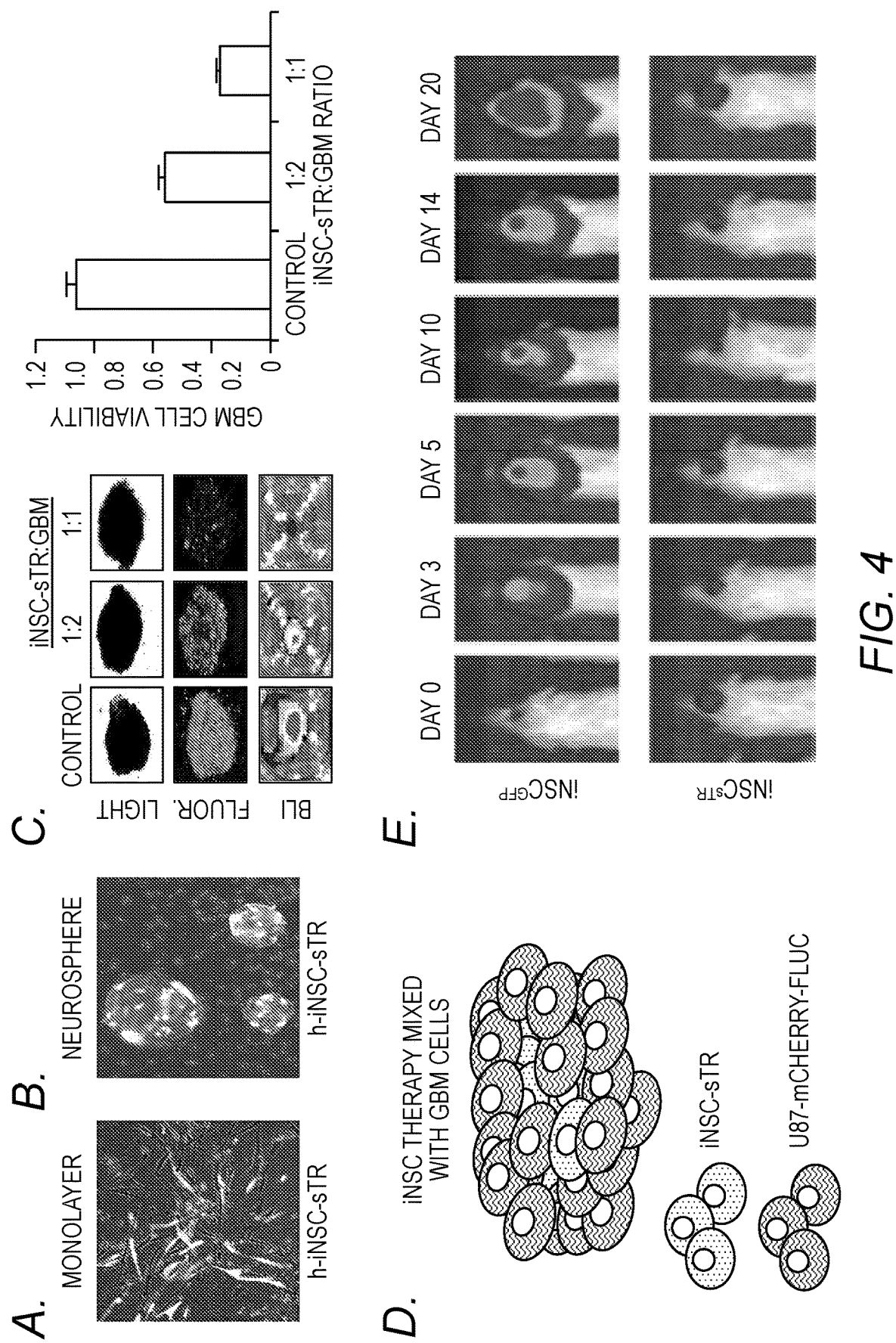
FIG. 4. h-INSC-mediated TRAIL therapy for solid GBM. (A-B) Representative fluorescent photomicrographs depicting the growth of h-iNSCs engineered to secrete the pro-apoptotic agent TRAIL and grown in a monolayer (A) or as floating neurospheres (B). (C) Images and summary data of 3D suspension cultures showing the viability of mCherry+ human U87 GBM spheroids mixed with therapeutic h-iNSC-sTR or control cells at ratio of 1:2 or 1:2. GBM spheroid viability was determined by luciferase imaging 48 hrs post-treatment. (D) h-iNSC-sTR therapy for solid GBM was performed by xenografting a mixture of h-iNSC-sTR and U87 GBM cells into the parenchyma of SCID mice. (E-F) Representative BLI images (E) and summary data (F) demonstrating the inhibition of sold U87 GBM progression by h-iNSC-sTR therapy compared to control-treated mice. (G) Kaplan-Meier curved demonstrating the extension in survival in h-iNSC-sTR-treated animal compared to h-iNSC-control. (H) Representative images demonstrating the expression of cytotoxic, differentiation, and pluripotency markers in h-iNSC-sTR following therapy. A subset of animals were sacrificed 14 days after therapy, and brain sections were stained with antibodies against nestin, TRAIL, GFAP, Tuj-1, Oct-4, or TRA-160 and the co-localization between staining and GFP+h-iNSC-sTR was visualized.
Figure 4:
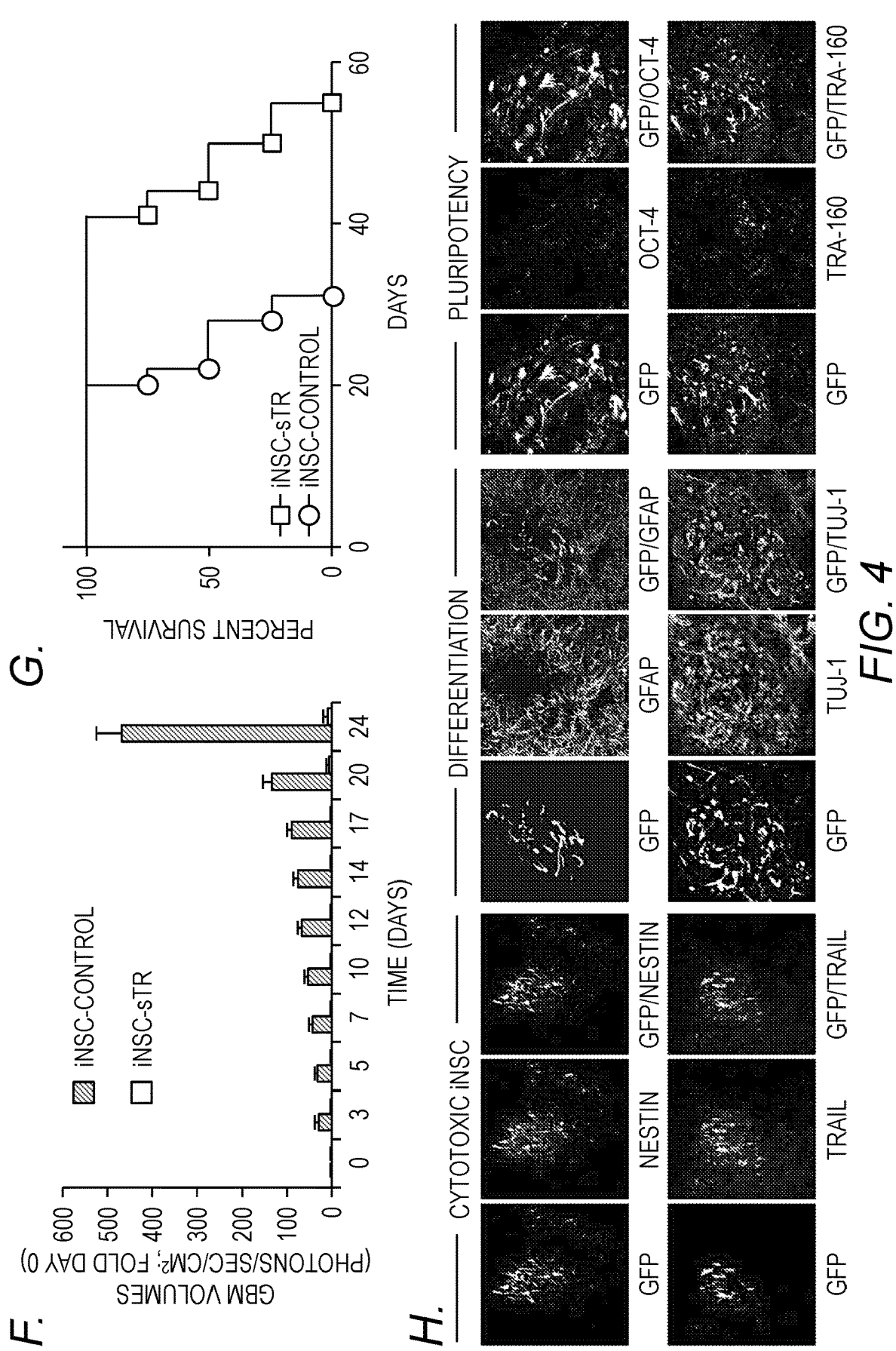

To investigate the therapeutic efficacy of h-iNSC-based GBM treatment, we first engineered h-iNSCs to express a secreted variant of the pro-apoptotic molecule TNFα-related apoptosis-inducing ligand (TRAIL; diTR) in frame with Gaussia luciferase and upstream of an IRES-GFP element (iNSC-diTR). Anti-cancer effects of TRAIL when delivered from engineered cell carriers were established previously; therefore it is the ideal tumoricidal molecule for characterizing new h-iNSC delivery vehicles. Robust expression of the GFP reporter was detected following transduction of the h-iNSCs (FIG. 4A). We observed that h-iNSC-diTR efficiently formed neurospheres when cultured in suspension (FIG. 4B), and displayed proliferative capacity and passage numbers equivalent to unmodified cells (data not shown). Nestin expression and differentiation capacity were the same as observed in previous engineered and not engineered h-iNSC, suggesting that modification of h-iNSCs with TRAIL does not interfere with their properties as stem cells.

To evaluate the anti-GBM efficacy of engineered h-iNSCs, h-iNSC-diTR or control iNSC-GFPRL were co-cultured at different ratios with human GBM cells expressing mCherry and firefly luciferase (mC-FL). In order to mimic the in vivo characteristics, GBM and h-iNSC were mixed and cultured in three-dimensional levitation system for 48 hours. Fluorescence and BLI revealed a significant reduction in the viability of GBMs co-cultured with h-iNSC-sTR. This reduction was significantly greater if a higher h-iNSC:GBM ratio was used (FIG. 4C).

h-iNSC Secretion of a Pro-Apoptotic Agent Reduces Solid GBM.

To test the in vivo efficacy of h-iNSC-sTR based therapy, we determined the effects of h-iNSC-sTR treatment on solitary human GBMs. Human U87 GBM cell expressing mC-FL were implanted intracranially with iNSC-sTR or control iNSC-GFP (FIG. 4D) and tumor volumes were followed using serial bioluminescence imaging. We found that h-iNSC-sTR treatment induced a statistically significant reduction in tumor growth by day 3 and decreased GBM volumes 50-fold by day 24 (FIG. 4F). In addition, h-iNSC-sTR-treated animals survived more than 51 days, while control animal succumbed to GBM growth in only 25 days (FIG. 4G). IHC examination of mouse brains showed a robust expression of TRAIL by the h-iNSC-sTR after two weeks. The h-iNSC-sTR in the GBM were positive for the expression of the Nestin and Tuj-1, and negative for GFAP and pluripotency markers Oct-4 and TRD-160 (FIG. 4H).

Efficacious Treatment of Malignant and Invasive GBM CD133+ Using Tumoricidal iNSCs.

Figure 5:
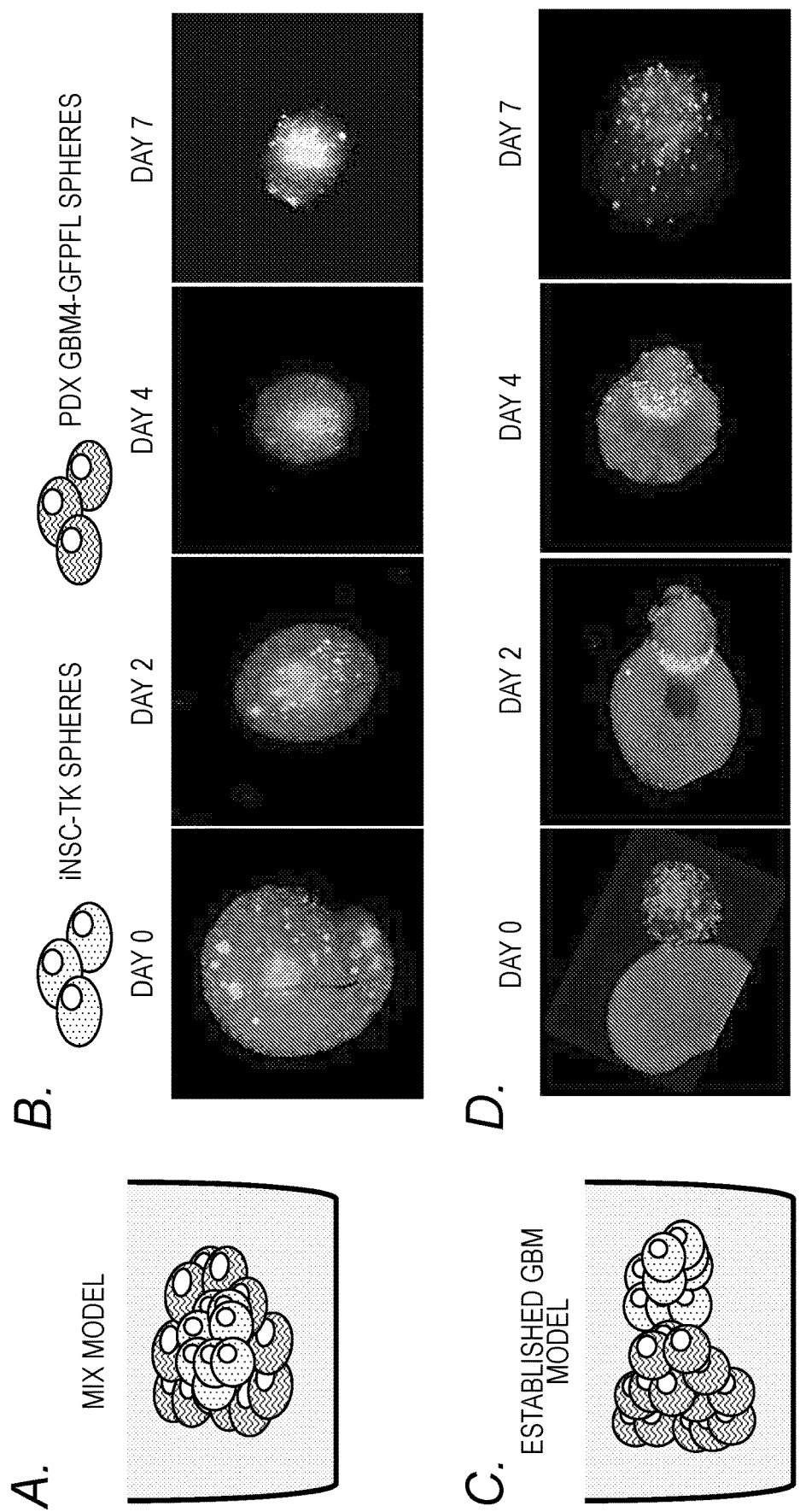
FIG. 5. h-iNSC prodrug/enzyme therapy for human patient-derived GBMs. (A-D) The anti-tumor effects of h-iNSC-TK therapy were determined in two different 3D culture models. h-iNSC-TK were either mixed with GFP+ GBM4 patient-derived GBM cells (A, B) or seeded adjacent to established GBM4 spheroids (C, D) and GCV was added to initiate tumor killing. Serial fluorescent images showed the time-dependent decrease in GBM4 spheroid volume by h-iNSC-TK/GCV therapy. (E) Summary graph demonstrating the reduction in GBM4 spheroid volume over 7 days by h-iNSC-TK/GCV therapy. (F-J) h-iNSC-TK therapy was assessed in vivo by injecting h-iNSC-TK cells into GBM4 tumors established 10 days earlier in the brain of mice (F). Serial BLI showed the progression of GBM4 tumors was significantly inhibited by h-iNSC-TK/GCV therapy (G). Kaplan-Meier survival curves demonstrating the survival of mice bearing GBM4 tumors treated with h-iNSC-TK/GCV therapy or control h-iNSCs (H). (I-J) Representative whole-brain and high-magnification images showing GBM4 volumes and h-iNSC-TK distribution 21 days after delivering h-iNSC-control (I) or h-iNSC-TK (J) into established GBM4 tumors. A large GBM4 tumor was present in the control-treated animals and only a small GBM4 foci was detected in the h-iNSC-TK-treated brain.
Figure 5:
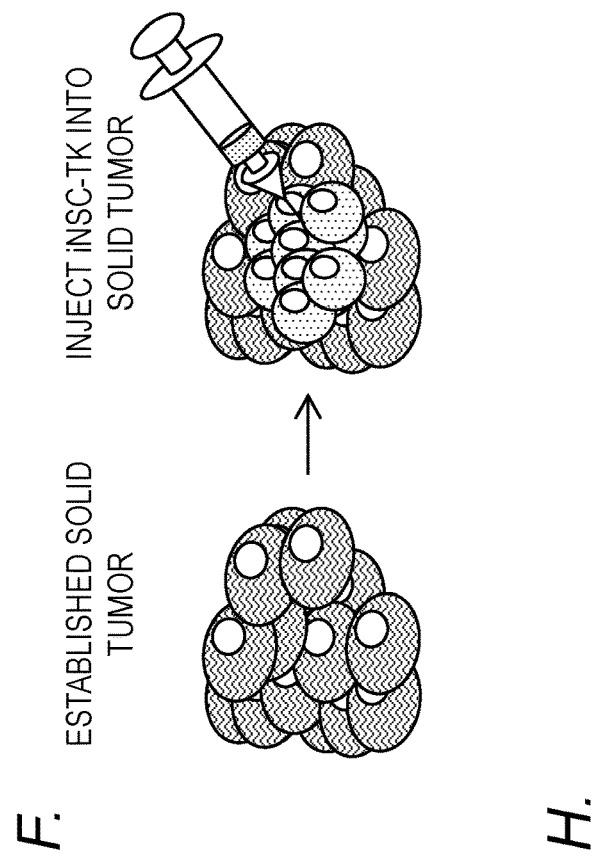
Figure 5:
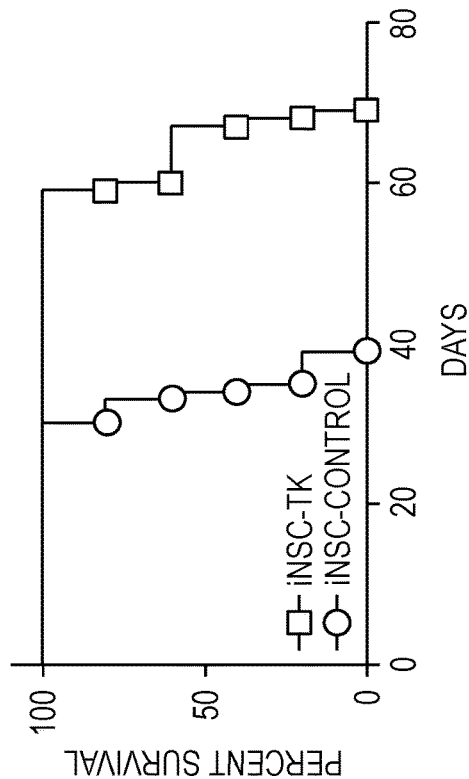
Figure 5:
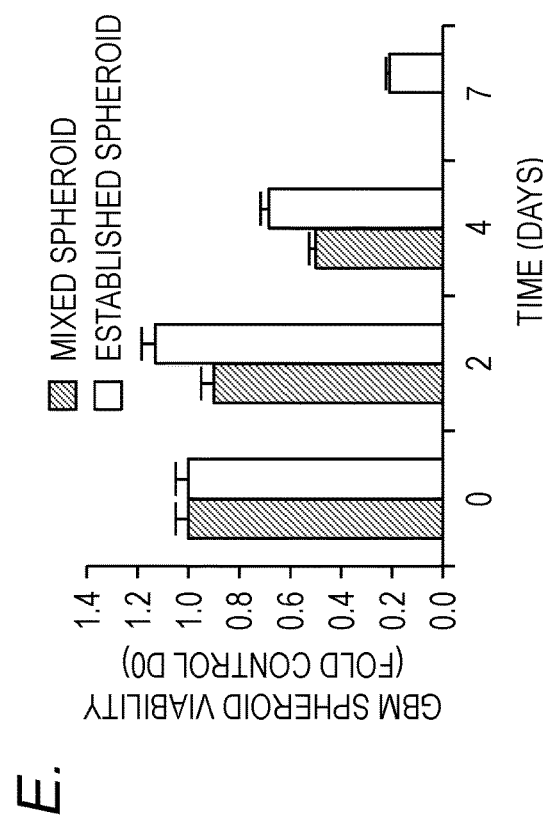
Figure 5:
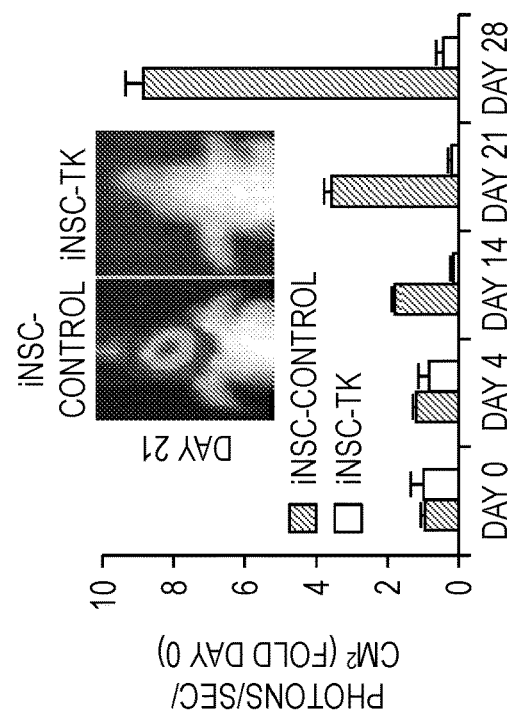

To determine the efficacy of h-iNSC prodrug/enzyme therapy for patient-derived CD133+ human GBM-initiating cells, we co-cultured GBM4 cells expressing GFP and firefly luciferase (GBM4-GFPFL) with h-iNSC expressing a tri-functional chimeric reporter including Rluc, RFP and thymidine kinase (TK) activities, to generate h-iNSC-TK. The thymidine kinase encoded by herpes simplex virus (HSV-TK) was used in the first cell suicide gene therapy proof of principle and still is one of the most widely used systems in clinical and experimental applications. GBM4-GFPFL and h-iNSC-TK were co-cultured in three-dimensional levitation system in two different models. The first model (FIG. 5A) the two cell types were mixed and cell survival monitored over time by fluorescence (FIG. 5B). The second model, the two cell types were cultured side by side to mimic the treatment of an established GBM (FIG. 5C). Cell survival was monitored over time by fluorescence (FIG. 5D). In both cases, a significant reduction of the GBM survival was observed over time, being more significant in the mixed model (FIG. 5E).

We next determined the efficacy of h-iNSC-TK therapy in vivo on established GBM4 by implanting GBM4-GFPFL cancer cells into the parenchyma of mice. Three days later, h-iNSC-TK or control cells were administered directly into the established tumors (FIG. 5F). Serial bioluminescence imaging showed that h-iNSC-TK treatment attenuated the progression of GBM4 tumors, reducing tumor burden by 9-fold compared to control 28 days after injection (FIG. 5G). h-iNSC-TK therapy also led to a significant extension in survival as h-iNSC-TK treated animals survived an average of 67 days compared to only 37 days in control-treated mice (FIG. 5H). Post-mortem IHC verified the significant reduction in tumor volumes by h-iNSC-TK injection (FIG. 5I-5J). Together, these results show that h-iNSC-TK therapy has significant therapeutic effects against malignant and invasive GBM and markedly prolongs the survival of tumor-bearing mice.

Intracavity h-iNSC-TK Therapy Inhibits Surgically Resected GBM Recurrence.

Figure 6:
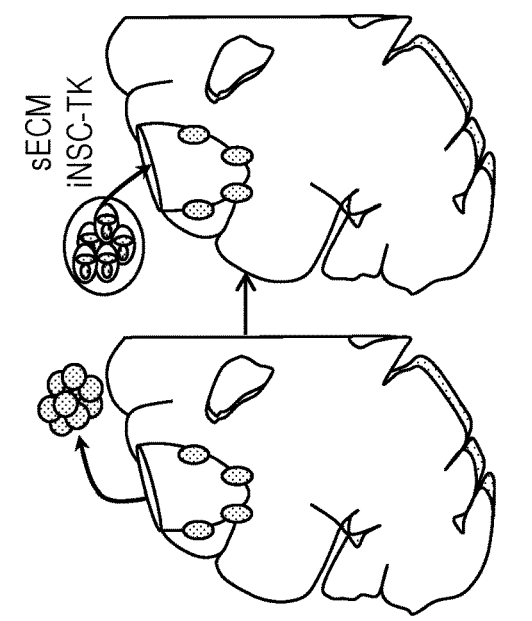
FIG. 6. Intracavity h-iNSC-TK therapy for surgically resected diffuse GBMs. (A-C) 3D suspension cultures were used to determine the migration and anti-tumor efficacy of synthetic extracellular matrix (sECM)-encapsulated h-iNSC-TK against patient-derived GBM8 spheroids (A). h-iNSC-TK encapsulated in sECM were found to migrate from the matrix and populate GBM8 spheroids 3 days after seeding (B). Representative images and summary data demonstrated that h-iNSC-TK encapsulated in sECM significantly reduce the volume of GBM8 spheroids compared to control-treated spheroids (C). (D) To mimic clinical h-iNSC therapy for surgically resected GBM, h-iNSC-TK were encapsulated in sECM and transplanted into the surgical cavity following resection of diffuse patient-derived GBM8 tumors expressing mCherry-FLuc. (E) Representative images and summary data of serial imaging demonstrating the significant inhibition in tumor recurrence following intra-cavity h-iNSC-TK therapy for post-operative minimal GBM8 tumors. (F) Kaplan-Meier survival curves of mice that underwent surgical resection of diffuse GBM8 patient-derived tumor cells treated with control h-iNSC or h-iNSC-TK encapsulated in sECM and transplanted into surgical cavity.
Figure 6:
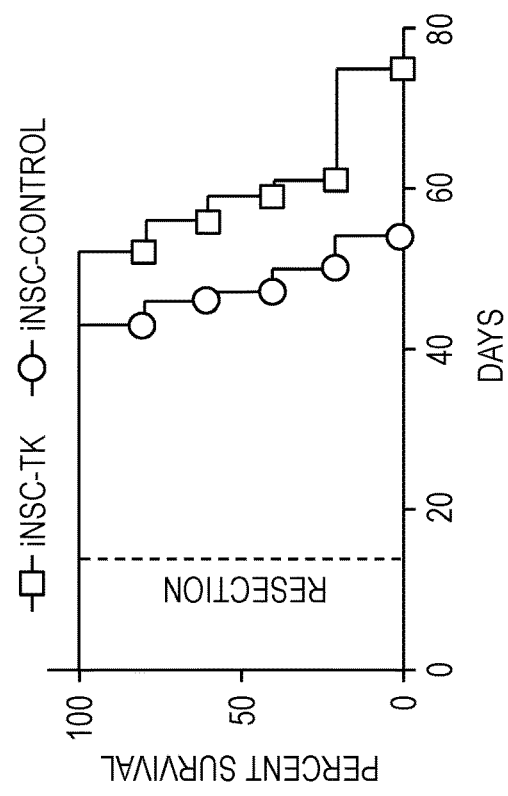
Figure 6:
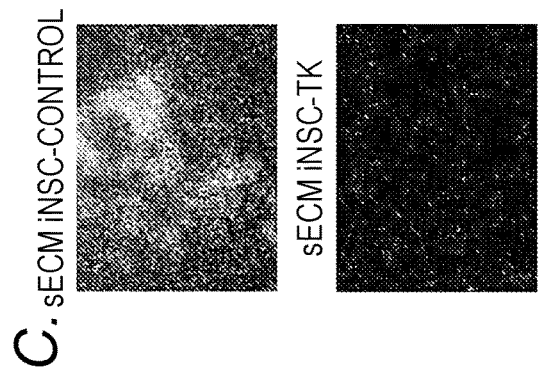
Figure 6:
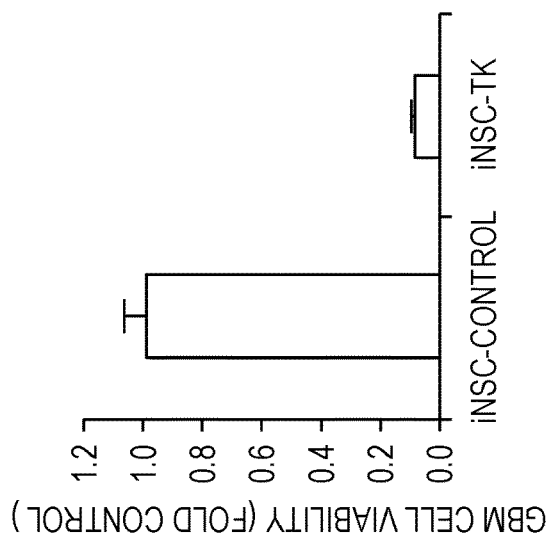
Figure 6:
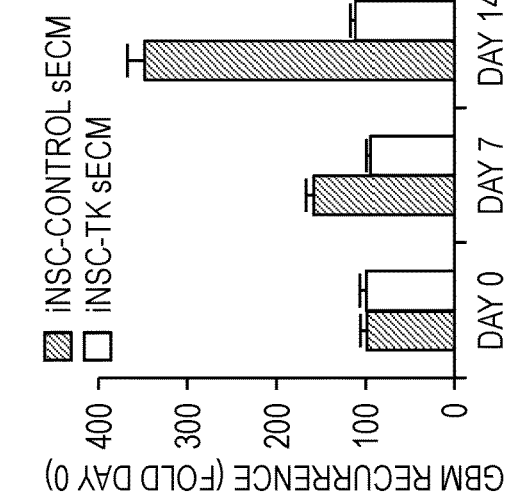
Figure 6:
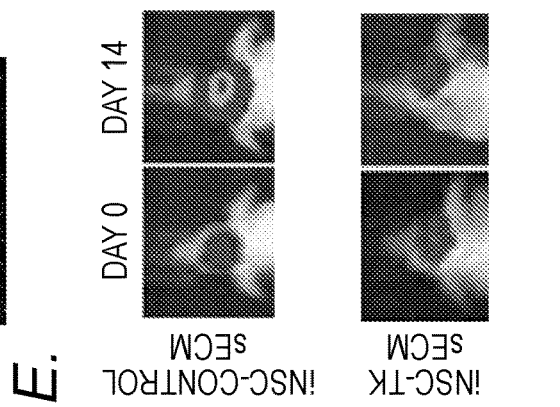

Surgical resection is part of the clinical standard of care for GBM patients. We previously discovered that encapsulation of stem cells is advantageous for intracavity therapy to effectively suppress GBM recurrence. To determine the efficacy of h-iNSC therapy encapsulated in synthetic extracellular matices (sECM), we co-cultured GBM-8 GFPFL (patient-derived CD133+ human GBM-initiating cell) with h-iNSC-TK embedded in HLA hydrogels (FIG. 6A). We found that mCherry+h-iNSCs migrated from the sECM matrix and populated GFP+ GBM8 spheroids within 3 days. Additionally, sECM/h-iNSC-TK therapy dramatically reduced the viability of GBM8 spheroids in 3 days.

To mimic h-iNSC therapy for surgically resected human GBM patients, we tested h-iNSC-TK therapy against highly diffuse patient-derived GBM8 cells in a mouse model of GBM resection (FIG. 6D). h-iNSC-TK embedded in HLA were transplanted into the surgical resection cavity following GBM debulking. Serial bioluminescence imaging showed that h-iNSC-TK therapy attenuated the recurrence of GBM8 tumors, reducing tumor burden by 350% compared to control 14 days after implantation (FIG. 6E). h-iNSC-TK therapy also led to a significant extension in survival as h-iNSC-TK treated animals survived an average of 59 days compared to 46 days in control-treated mice (FIG. 6E).

Example 2: Alternative Media for Rapid Transdifferentiation of Human Skin Cells

Transdifferentiation of human skin cells was performed as above in Example 1, but in place of the STEMdiff™ Neural Progenitor Basal Medium was a 1:1 mixture of N-2 medium and B-27 medium as follows. Chemicals were purchased from Gibco® (Invitrogen Corporation, Carlsbad, Calif.), Sigma (Sigma-Aldrich, St. Louis, Mo.) or Selleck Chemicals (Houston, Tex.) as indicated.

N-2 Medium:
DMEM/F12 (Gibco®)
1×N2 supplement (Gibco®)
5 µg/ml insulin (Sigma)
1 mM L-glutamine (Gibco®)
1 mM Glutamax (Gibco®)
100 µM MEM non-essential amino acids (NEAA) (Gibco®)
100M beta-mercaptoethanol (bME)
B-27 Medium:
Neurobasal medium (Gibco®)
1×B-27 supplement (Gibco®)
200 mM L-glutamine (Gibco®)
To the 1:1 mix was added bovine serum albumin (BSA, Sigma) to a final concentration of 5 µg/ml.
This medium was supplemented with the following: SB431542 (Selleck Chemicals) to a final concentration of 10 µM; LDN193189 (Selleck Chemicals) to a final concentration of 100 nM; all trans retinoic acid to a final concentration of 10 µM (Sigma); and CHIR99021 (Selleck Chemicals) to a final concentration of 3 µM.
Using this media, nestin+ iNSCs were generated when used with the Sox2 transduction.
The medium may also be made to include Insulin (25 µg/ml), Transferrin (100 µg/ml), Sodium selenite (30 nM), and/or cAMP (100 ng/ml).

Example 3: Transplanting Cytotoxic Stem Cells in Fibrin Sealant Increases Retention and Inhibits Post-Surgical Glioblastoma Recurrence Tumor-homing cytotoxic stem cell (SC) therapy is entering human patient testing for treatment of the incurable brain cancer glioblastoma (GBM). However, pre-clinical evidence suggests this strategy may suffer from poor retention and efficacy against surgically resected GBM. Here, we provide the first data that the clinically utilized fibrin glue TISSEEL (Baxter Healthcare Corporation) increases the persistence of human cytotoxic SCs within the surgical cavity and significantly suppresses regrowth of post-surgical minimal GBM in mice. When drug-releasing human mesenchymal stem cells (hMSCs) were encapsulated in fibrin matrices, in vitro studies showed the hMSCs proliferated within the fibrin and rapidly migrated out, homing to co-cultured human GBM cells. In mouse models of GBM resection, therapeutic hMSCs transplanted into the post-surgical cavity were found to be retained 2-fold greater and persist 3-fold when encapsulated in TISSEEL compared to the clinical standard of direct injection. hMSCs releasing the cytotoxic agent TRAIL (hMSC-sTR) encapsulated in TISSEEL significantly reduced the viability of human GBM spheroid in 3-dimensional cultures, and regressed established human GBM xenografts 3-fold in 11 days. Mimicking therapy for post-surgical human GBM, intracavity TISSEEL/hMSC-sTR therapy reduced post-surgical GBM volumes 6-fold, increased time to recurrence 4-fold, and increased median survival from 15 days to 36 days after surgery compared to control-treated animals.
Materials and Methods
Cell lines and viral vectors. U87 human GBM cells (American Type Culture Collection, Manassas, Va.) and human MSC (American Type Culture Collection, Manassas, Va.) were cultured in DMEM (Invitrogen) supplemented with 10% heat-inactivated fetal bovine serum, 100 µg/mL penicillin, 100 µg/mL streptomycin. Several different lenti-viral vectors were used in these studies: 1) fluorescent and bioluminescent reporters: mCherry-FLuc, GFP-RLuc 2) therapeutic vector: LV-sTR contains secreted TRAIL, 3) LV-diTR encodes a fusion of sTR and *Gaussia* luciferase. Vectors were generated as described above, and sTR-containing vectors have IRES-GFP (internal ribosomal entry sites-green fluorescent protein) elements in the backbone as well as CMV-driven puromycin element. All LV constructs were packaged as LV vectors in 293T/17 cells using a helper virus-free packaging system as described previously[15,16]. U87 and MSC were transduced with LVs at varying multiplicity of infection (MOI) by incubating virions in a culture medium containing 5 µg/ml protamine sulfate (Sigma) and cells were visualized for fluorescent protein expression by fluorescence microscopy. TISSEEL Fibrin Sealant (Baxter Healthcare Corp., Deerfield, Ill.) was purchased from the University of North Carolina Hospitals and Clinics.
Seeding in Fibrin.
Fibrin patches were created under sterile conditions using Sealer and Thrombin preparations from TISSEEL®. To prepare the fibrin scaffolds, eight microliters of Sealer solution (67-106 mg/mL fibrinogen) were mixed with 100,000-500,000 hMSCs. Eight microliters of the Thrombin (400-625 units/mL thrombin) preparation was added to initiate gelation and physically mixed using a micropipette tip for 30 seconds to create droplets. Fibrin patches were created by flattening the droplets through physical pressure to a thickness of approximately 1 mm. Fibrin patches loaded with cells were then cultured under standard conditions with supplemented DMEM (10% FBS, 1% P/S, 1% L-glutamine).
Cell Viability and TRAIL Secretion In Vitro.
To define the viability of hMSCs in scaffolds, hMSC-GFPFLuc ($1\times10^5$ cells/scaffold) were encapsulated in fibrin droplets as described or seeded directly into wells without encapsulation. On days 0, 2, 5 and 9 after seeding, high-resolution fluorescent images were captured using an Olympus and bioluminescent images were captured by incubating cells in D-luciferin (1.5 µg/ml) and measuring luciferase activity using an IVIS' Kinetic imaging system (Perkin Elmer, Waltham, Mass.). Cell growth was determined by quantification of the fluorescent signal intensity using NIH Image or from luciferase activity using the IVIS' Kinetic image analysis software and expressed as $p/sec/cm^2/sr$. Arbitrary color bars represent standard light intensity levels (blue=lowest; red=highest). Each experiment was performed in triplicate.
To determine TRAIL secretion, hMSC-diTR ($1\times10^5$ cells/scaffold) were seeded as describe above. On days 0, 2, 5 and 9 after seeding, equal volumes of cell culture medium containing the secreted diTR fusion proteins was collected, incubated with coelenterazine (1 g/ml), and photon emission was determine in a luminometer.
Time-Lapse Imaging and Motion Analysis.
A 0.6% agarose mold was prepared to mimic brain tissue. 3 ml of the agarose solution was added to each well of 6-well culture plates and allowed to solidify. A 2 ml aspirating pipette attached to a vacuum was used to create cavities in the agarose ~500 µm apart. hMSC-GFPRluc embedded in Fibrin were placed in one of the agarose cavities. Human U87-mCFLuc cells were seeded in the adjacent hole, or the cavity was left empty and the wells were filled with media. The cell/agarose system was placed in a VivaView live cell imaging system (Olympus) and allowed to equilibrate. Fluorescent images were captured at 10× magnification every 20 minutes for 64 hours in 6 locations per well (to monitor sufficient cell numbers). Experiments were conducted in triplicate. NIH Image was then used to generate movies and to define the migratory path of MSCs, the directionality of migration, and the velocity of MSC migration using the "Manual Tracking" and "Chemotaxis Tool" plugins.

Co-Culture Viability Assays.

hMSC-sTR or hMSC-GFRLuc ($3\times10^5$) were seeded in fibrin scaffolds as described above. Human U87, Ln229, and U251 GBM cells expressing mCherry-FLuc ($2\times10^5$ cells) were plated around the hMSCs seeded in fibrin. GBM cell viability was measured at different time points (0, 2, 4 and 6 days) by quantitative in vitro bioluminescence imaging as described previously[16]. 3-D co-culture assays were preformed by forming 3-D cell spheroids using the bio-assembler kit (Nano3D Biosciences, Houston, Tex.) according to manufactures specifications. Briefly, GBM cells were treated overnight with 50 μl ml$^{-1}$ of nanoshuttle magnetic particles. The next day, cells were detached with trypsin and plated in an ultra-low attachment 6-well plate. A magnetic driver of 6 neodymium magnets (field strength=50 G) were placed atop the well plate to levitate the cells to the air-liquid interface and cultured for an additional 18-24 hrs to form spheroids. hMSC-sTR or hMSC-GFPRLuc were labeled with nanoshuttle and encapsulated in fibrin. To create 3-D co-culture suspensions, the GBM spheroids and hMSC/fibrin were placed together in low adhere wells and a magnet was placed over the low-attachment plate. GBM cell viability was determined by luciferase assay 24 hrs later.

In Vive Models.

Stem cell persistence: To determine the persistence of fibrin-encapsulated stem cells in the post-surgical GBM cavity, U87-mCFLuc were harvested at 80% confluency. Nude mice (6-8 weeks of age; Charles River Laboratories, Wilmington, Mass.) were implanted stereotactically with the U87mCFLuc ($5\times10^5$ cells) in the right frontal lobe 2 mm lateral to the bregma and 0.5 mm from the dura (n=8). For tumor resection, the intracranial xenograft was identified using mCherry fluorescence. The U87-mCFLuc tumor was surgically excised using a combination of surgical dissection and aspiration under mCherry excitation. Fluorescent images of mCherry+ GBM were continuously captured to assess accuracy of image-guided surgical resection. Following tumor removal, hMSC-GFPFLuc ($1\times10^6$ cells) were divided into two groups and: 1) suspended in 10 μls of saline and directly injected into the walls of the cavity, or 2) suspended in 6 μls of fibrin, seeded into the resection cavity, and gelated by the addition of 5 μls of thrombin. hMSC levels were determined by serial bioluminescence imaging. Mice were injected intraperitoneally with D-luciferin (4.5 mg/ml in 150 μls saline) and photon counts were measured 5 minutes after injection over 7 mins using the IVIS' Kinetic imager. Initial hMSC retention was determined by imaging 3 hours post-implantation. hMSC survival was determined subsequent imaging 2, 4 6, 10, 14, and 21 days post-implantation. Photon emission was determined using the IVIS® Kinetic imaging analysis software and expressed as p/sec/cm$^2$/sr relative to day 0. All experimental protocols were approved by the Animal Care and Use Committees at The University of North Carolina at Chapel Hill and care of the mice was in accordance with the standards set forth by the National Institutes of Health *Guide for the Care and Use of Laboratory Animals*, USDA regulations, and the American Veterinary Medical Association.

Solid Tumor Therapy:

Nude mice were anesthetized and U87 GBM cells ($3\times10^5$ cells) were injected into the para-spinal space of the mouse in 100 μl of PBS (2 independent injection sites per animal). One week later, fibrin scaffolds bearing hMSC-sTR or control hMSC-GFPRluc were surgically implanted over the established tumors. Tumor growth was determined by serial FLuc imaging and image analysis as described above, expressed as p/sec/cm$^2$/sr relative to day 0.

Post-Surgical Minimal GBM Therapy:

To investigate the efficacy of hMSC-sTR encapsulated in fibrin for treatment of post-operative GBM, U87mCFLuc ($5\times10^5$ cells) were implanted into the frontal lobe of mice as described above. Established GBMs were surgically resected under image-guidance and hMSC-sTR or hMSC-GFPRLuc in fibrin were seeded into the resection cavity and matrix was polymerized by the addition of thrombin. Tumor regrowth was monitored by serial Fluc imaging as described earlier.

Tissue Processing.

Immediately after the last imaging session, mice were sacrificed, perfused with formalin, and brains extracted. The tissue was immediately immersed in formalin. 30 μm coronal sections were generated using a vibrating microtome (Fisher). Sections were washed three times with PBS and visualized using a confocal microscope (Olympus). In a subset of mice, brains were isolated, incubated with or without D-luciferin, and ex vivo whole-brain bioluminescent and fluorescent imaging was performed using the IVIS' Kinetic system.

Statistical Analysis.

Data were analyzed by Student t test when comparing 2 groups and by ANOVA, followed by Dunnetts post-test when comparing greater than 2 groups. Data were expressed as mean±SEM and differences were considered significant at $P<0.05$. Survival times of mice groups (n=5/group) were compared using logrank test.

3. Results

Generation and Characterization of Fibrin Scaffolds Bearing Engineered Stem Cells.

Fibrin Scaffolds do not Affect Proliferation or Drug Release.

Figure 7:
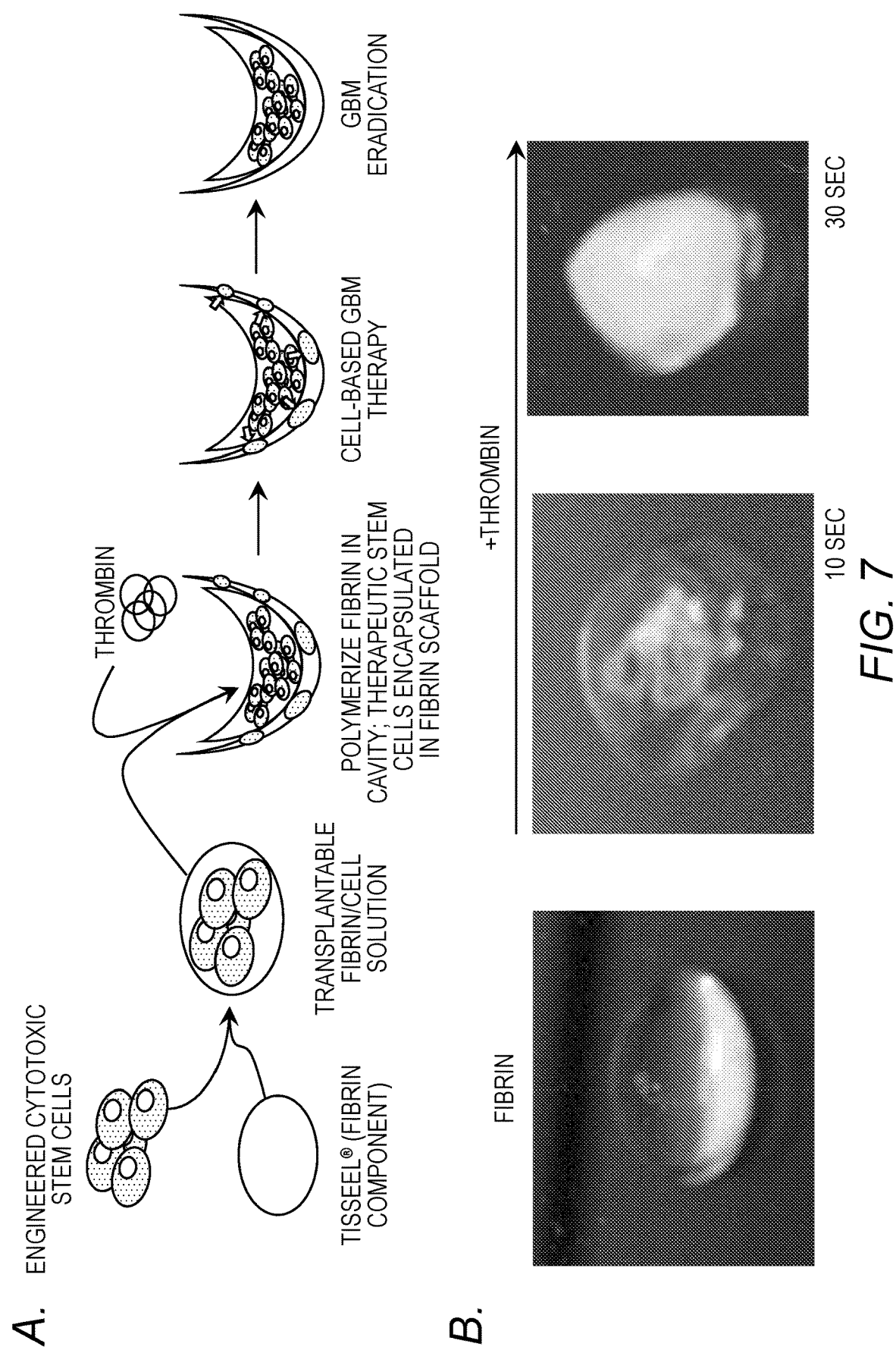
FIG. 7. Characterization of engineered hMSCs on Fibrin. (A) Schematic representation of a novel cancer therapy using fibrin to deliver drug releasing stem cells into the GBM resection cavity. This strategy begins with mixing cytotoxic stem cells with the fibrin component of TIS-SEEL®. Following surgical GBM resection, the post-operative cavity is filled with the fibrin/stem cell mixture that is polymerized by the addition of thrombin. The fibrin scaffold retains the cytotoxic stem cells in the cavity and allows the therapeutic stem cells to migrate to the GBM foci and deliver tumoricidal agents that will eradicate residual tumor. (B) Representative white-light images demonstrating the rapid gelation of fibrin by the addition of thrombin to create encapsulated cytotoxic stem cells. (C) Representative fluorescent and BLI depicting the growth of hMSC in fibrin over time. Fluorescent images are captured at 10× to depict cellular morphology and 2× to demonstrate overall cell growth. Simultaneous BLI was performed to validate cell volumes. (D) Summary graph comparing the growth and therapeutic protein release rates of hMSC-sTR cultured with or without Fibrin. (E) Summary data showing the levels of cytotoxic protein secreted by hMSC-diTR grown in different fibrin matrices or without scaffolds. "Droplet" formation was created by suspending and polymerizing stem cells in a droplet of fibrin. The "encapsulated patch" was created by encapsulating stem cells in a fibrin droplet that was pressed into a flat sheet. The "surface patch" was created by seeding stem cells onto the surface of a flattened fibrin scaffold. Secretion was determined by BLI on media samples collected 1, 3, and 6 days after seeding.
Figure 7:
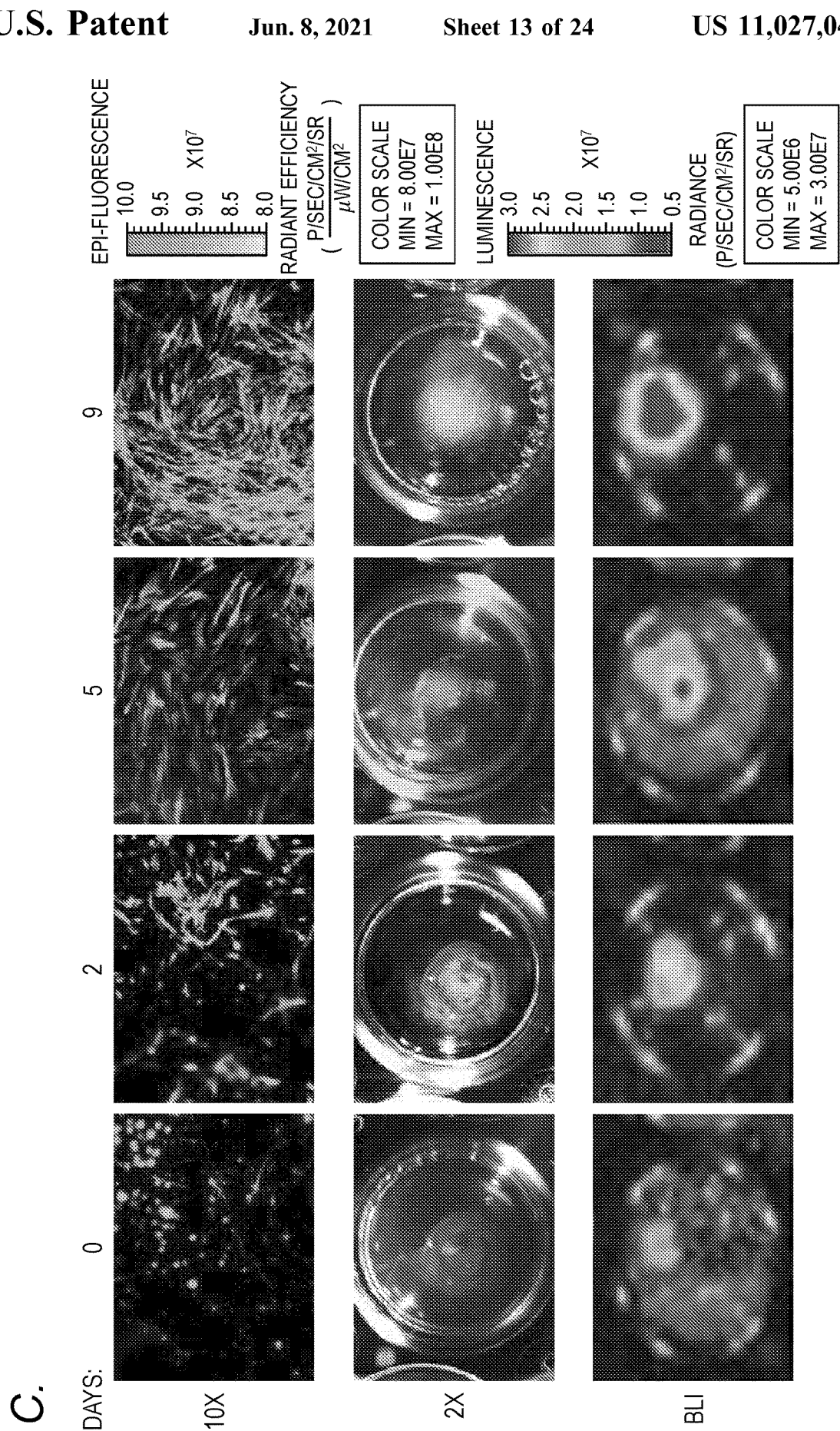
Figure 7:
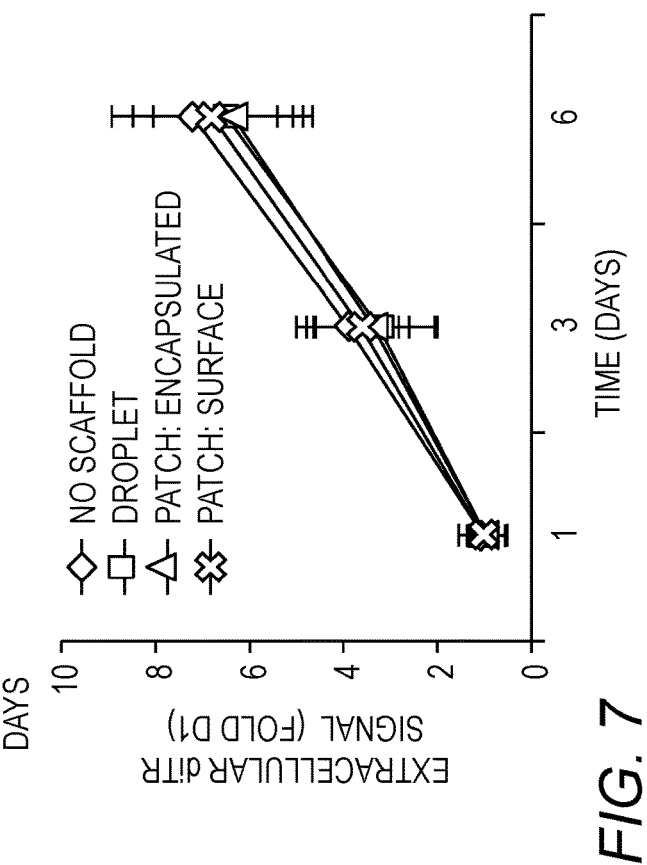
Figure 7:
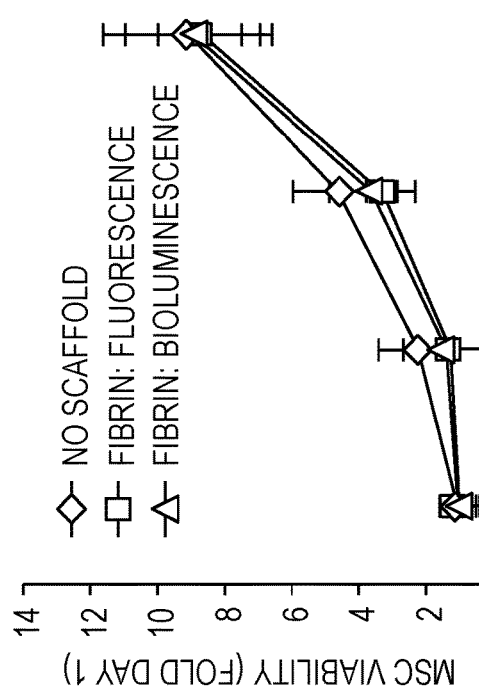
Figure 7:
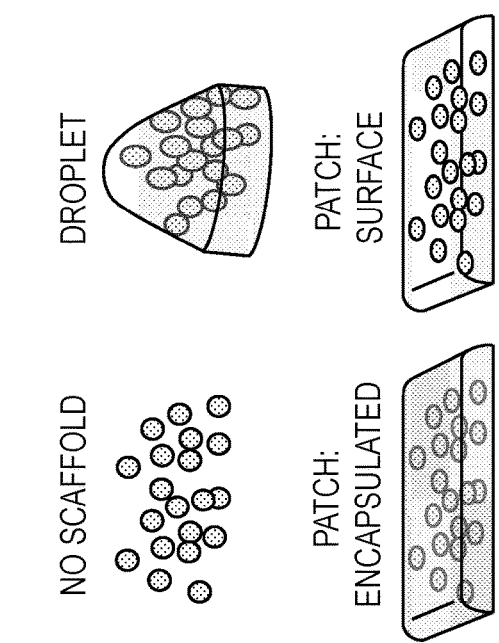

We sought to create a new transplant strategy where therapeutic stem cells were retained in the GBM surgical resection cavity using clinically compatible fibrin scaffolds (strategy outlined in FIG. 7A). Human mesenchymal stem cells (hMSCs) engineered to express GFP and firefly luciferase (hMSC-GFPFLuc) were resuspended in fibrin component of the medical-grade fibrin sealant TISEEL. Upon addition of thrombin, the matrix rapidly polymerized, encapsulating the hMSCs within the scaffold (FIG. 7B). Fluorescent and bioluminescent imaging (BLI) of these hMSC-GFPFluc-loaded fibrin scaffolds showed the stem cells proliferated in the matrix over nine days (FIG. 7C). Quantification showed the hMSC-GFPFLuc growth was equivalent between cells encapsulated in fibrin or grown without the matrix, suggesting the matrix had no effect on viability or proliferation (FIG. 7D). To investigate the impact of scaffold architecture on hMSC drug release, we engineered hMSCs with a diagnostic fusion between TRAIL and *Gaussia* luciferase (hMSC-diTR) that we have previously utilized to detect differences in drug release between stem cell types. Equal numbers of hMSC-diTR were cultured 1) without scaffolds, 2) encapsulated within a fibrin scaffold that was not mechanically altered, 3) within a fibrin scaffold that was mechanically flattened after being loaded with cells, or 4) seeded on the surface of a pre-fabricated flat scaffold. BLI of media samples collected 1, 3, and 6 days post-seeding demonstrated diTR secretion was equivalent in all groups (FIG. 7E), suggesting hMSC-diTR release was not inhibited by the presence of the scaffold, the shape of the scaffold, or encapsulation versus surface seeding.

hMSCs Migrate Out of Fibrin Scaffolds and Home to GBM Cells.

To study the migration and tumoritrophic homing of hMSCs seeded in fibrin scaffolds, we developed a novel strategy that combined time-lapse motion analysis with 3-dimensional (3-D) under-agarose migration systems. In this approach, a tissue culture dish is filled with a 0.6% agarose solution to mimic the composition of the brain. A cavity is created in the agarose and hMSC-GFPFLuc in fibrin scaffolds are seeded into the cavity. Human U87-mCFluc are seeded into a second cavity 500 μm away to establish a chemotactic signaling gradient. The system is placed in an incubator microscope and kinetic images are captured every 20 minutes for 64 hrs to define the migration of hMSCs on fibrin scaffolds and as they move off of fibrin scaffold through the agarose matrix towards the U87-mCFluc cells (outlined in FIG. 8A).

Figure 8:
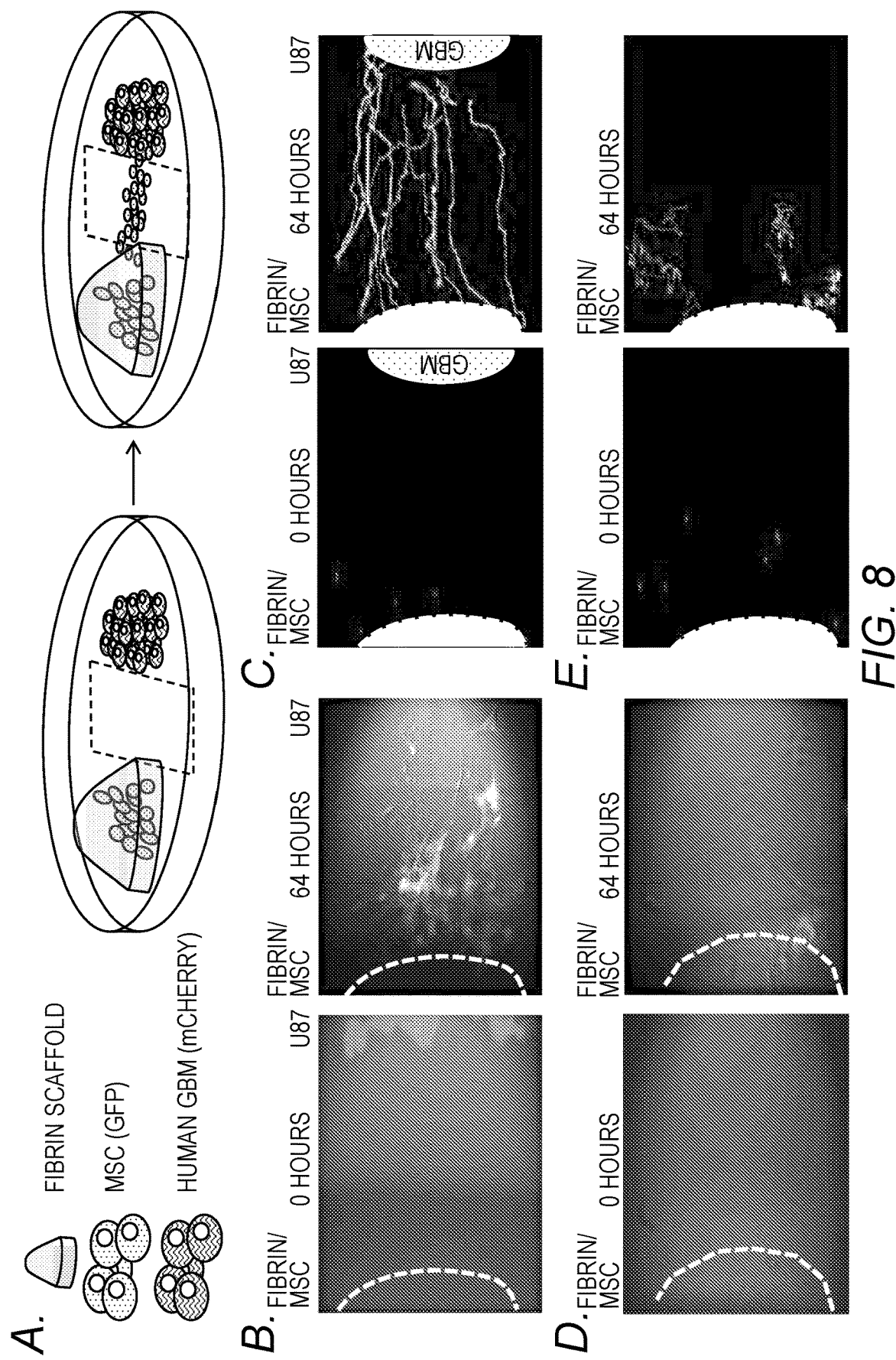
FIG. 8. The tumor-directed migration of hMSCs in Fibrin. The migration of fibrin-encapsulated stem cells to GBM cells was measured using time-lapse motion analysis and under-agar co-culture system. (A) Schematic depiction of the co-culture strategy. GFP+ stem cells were encapsulated in Fibrin and seeded into one well of an agar-filled culture dish. mCherry+U87 human GBM cells were seeded 500 µm away in an adjacent well. The cells were placed under a fluorescence microscope in an incubator and images were captured every 15 minutes for 64 hours. Image analysis software was then used to generate time-lapse movies, perform single-cell tracking, and quantify migratory direction, distance and velocity. The imaging field is depicted by the dotted blue line. (B) Summary images showing hMSCs (green) migrate out of fibrin and home to co-cultured GBM cells (red). (C) Single-cell analysis depicting the migratory path of hMSCs from fibrin scaffolds as they home to GBM cells over time. Each line depicts the path of one cell. (D) Fluorescent images and single-cell analysis (E) showing the random motion of hMSCs in fibrin when cultured in the absence of GBM cells. (F) Rosetta graphs demonstrating the directed migration hMSCs out of fibrin scaffolds when GBM are present and the random migration of hMSCs from fibrin in the absence of GBM cells. (G) Summary graphs showing the directionality, distance, and velocity of hMSCs in fibrin in the presence and absence of human GBM cells. In all panels, *P<0.01 vs. control and values are mean±SEM.
Figure 8:
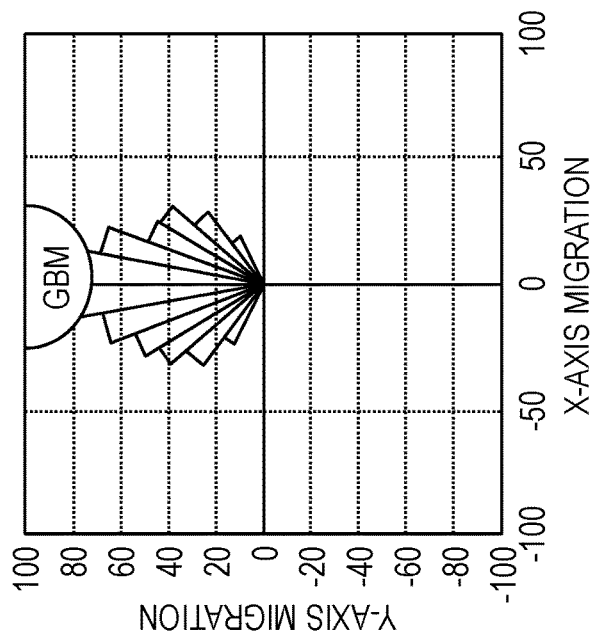
Figure 8:
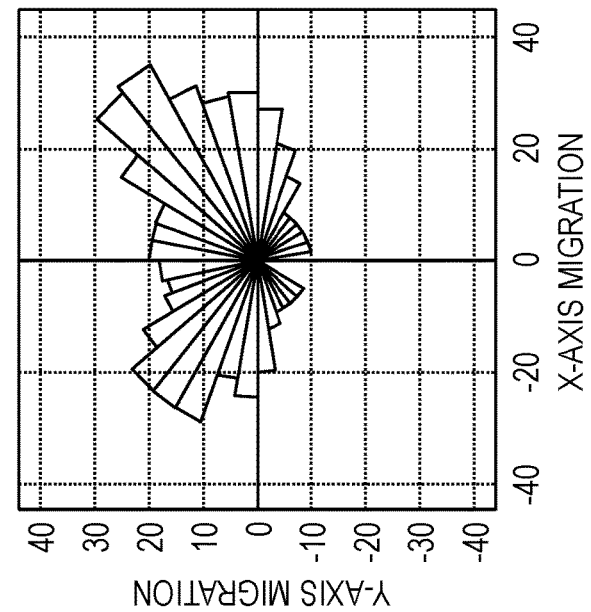
Figure 8:
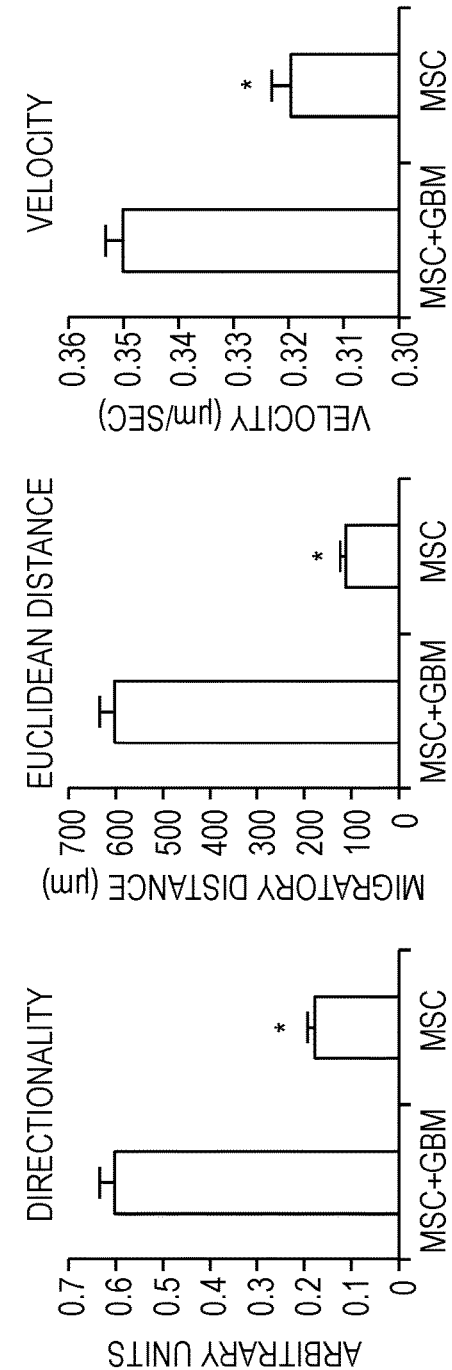

Using this strategy, time-lapse fluorescent imaging demonstrated that encapsulated hMSCs migrated out of the fibrin scaffolds and co-localized with co-cultured GBM cells (FIG. 8B). Single cell migratory path analysis showed that hMSCs selectively homed to the co-cultured GBM cells, reaching the cells in less than 64 hours (FIG. 8C). In contrast, hMSCs cultured without GBMs showed minimal migration from the scaffold (FIG. 8D), and migrated in a random non-directed pattern in the absence of GBM cells (FIG. 8E). Quantitative analysis and rosetta plots further confirmed the highly directional migration of hMSCs in the presence of GBM cells, with few cells migrating in the opposite direction of the GBM cells (FIG. 8F). Alternatively, hMSCs migrated in a random 360° pattern in the absence of GBM cells. The directionality of the migration of hMSCs seeded into the fibrin scaffolds was analyzed by calculating the ratio of Euclidian distance to overall accumulated distance, with perfect single direction movement yielding a ratio of 1.0 and perfectly non-directional movement yielding a ratio of 0.0. Using this analysis, hMSCs encapsulated in fibrin scaffolds showed an average migration directionality ratio of 0.63 when co-cultured with U87 cells (FIG. 8G), that was reduced to only 0.17 in the absence of tumor cells. Further analysis of single cell migration patterns demonstrated significantly increased average Euclidian distance migrated by hMSCs cultured in the presence of U87 cells (878.2 μm) as compared to those cultured in the absence of U87 cells (239.5 μm with a standard deviation of 118.4 μm). Lastly, no significant differences in average cell velocity as measured by single cell migration analysis was detected with hMSCs cultured in the presence of U87s versus in the absence of GBM cells.

The Retention and Survival of hMSC Encapsulated in Fibrin and Transplanted into the GBM Cavity.

Figure 9:
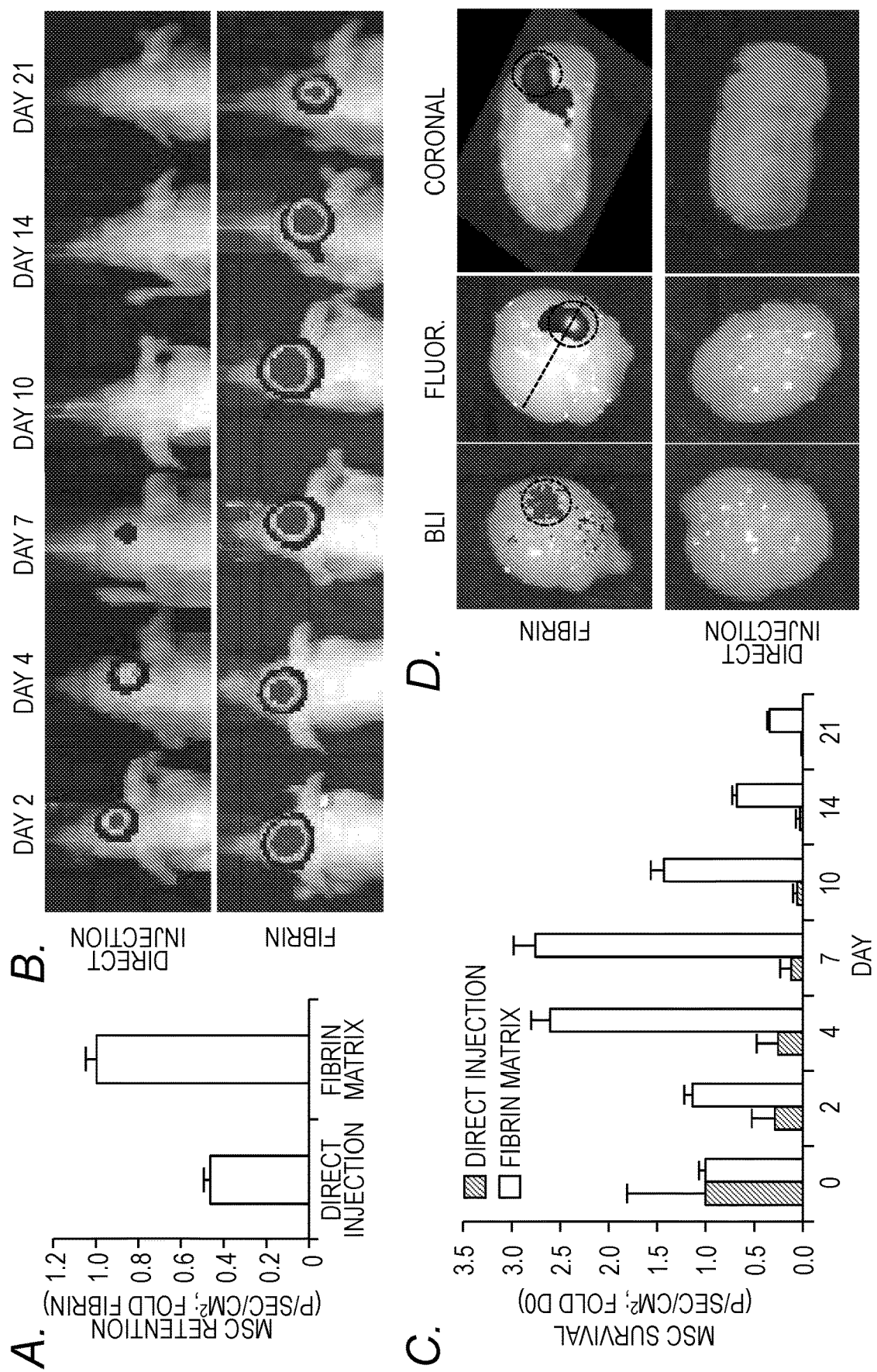
FIG. 9. Fibrin scaffolds improve the retention and persistence of cytotoxic hMSCs transplanted into the post-operative surgical cavity. (A) Summary graph demonstrating the retention of hMSCS in the post-surgical cavity transplanted by direct injection or in a fibrin matrix. Retention was determined by quantitative BLI to detect hMSC volumes 2 hrs. after transplant. (B-C) Representative images and summary data demonstrating the persistence of hMSCS transplanted into the resection cavity by direct injection or in fibrin matrix. BLI images were captured longitudinally on days 0, 2, 4, 7, 10, 14, and 21 post-transplant to track the levels of transplanted hMSCs. (D) Ex vivo fluorescent and BLI imaging of brains 21 days after transplanting hMSC-mCFL into the resection cavity via fibrin or direct injection. A hMSC-mCFL signal was detected in the fibrin-transplanted animals in both the dorsal view and coronal cross-sections, but no signal was detected in the direct injection brains. (E-F) Representative fluorescent images showing the presence of hMSC-mCFL in the parenchyma following delivery into the resection cavity in fibrin (E) or by direct injection (F). Whole brain photo-stitched images and 10× images are shown. * indicates the resection cavity. The arrows indicate the small deposit of hMSC-mCFL present in the direct injection brain.
Figure 9:
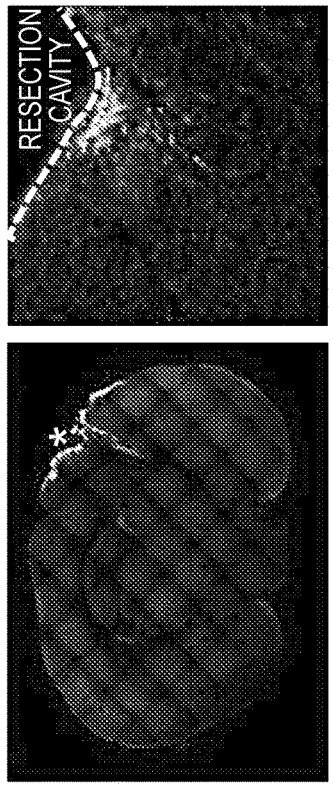

To determine the impact of fibrin encapsulation on intracavity stem cell persistence, we measured the retention and survival of engineered hMSCs transplanted into the GBM cavity with or without fibrin encapsulation using our mouse models of GBM resection. Established human GBM xenografts were surgically debulked. hMSC-mCFL were embedded in fibrin, seeded into the cavity, and polymerized by the addition of thrombin. Alternatively, equal numbers of hMSC-mCFL were directly injected into the walls of the surgical cavity in a subset of animals to mimic the scaffold-free transplant that is currently used in clinical GBM patient trials. Both hMSC-mCFL retention and survival in the post-operative cavity was significantly increased by fibrin encapsulation. Quantitative BLI 2 hrs post-implantation showed 48% more hMSC-mCFL were retained in the post-operative cavity by fibrin-based transplant compared to direct injection (FIG. 9A). Longitudinal BLI showed 61% of fibrin-encapsulated hMSC-mCFL persisted through 21 days in the cavity (FIG. 9B-9C). The fibrin matrix initially allowed the hMSC-mCFL to proliferate in the post-operative cavity, as the BLI signal increased 2.7-fold in 7 stay post-transplant before gradually declining. In contrast, hMSC-mCFL directly injected into the post-operative cavity were rapidly cleared from the cavity with only 19% of cells remaining at 7 days post-transplant and complete clearance by day 10 (FIG. 9B-9C). Ex vivo whole-brain fluorescent and BLI performed 21 days post-transplant confirmed the in vivo BLI. Significant photon emission was detected in the resection cavity of fibrin-encapsulated hMSC-mCFL group, while no BLI signal was detected in brains where hMSC-mCFL were directly injected (FIG. 9D). Interestingly, whole-brain cross-sectional analysis showed the hMSC-mCFL signal extended beyond the boarder of the resection cavity, suggesting hMSCs migrated from the cavity into the parenchyma. This was confirmed by high-resolution fluorescent imaging of tissue sections, where numerous mCherry+ hMSCs were found to line the tissue adjacent to the resection cavity in fibrin-encapsulated brains (FIG. 9E). Directly injected hMSCs were detected in tissue sections, but the few cells were confined to a small single site (FIG. 9F). Together, these data provide the first demonstration that fibrin encapsulation improves the retention and survival of engineered stem cells into the GBM resection cavity, while allowing stem cells to migrate from the matrix into the parenchyma.

Anti-Tumor Efficacy

Efficacy of Therapeutic hMSCs in Fibrin Against 3-D Human GBM Spheroids.

Figure 10:
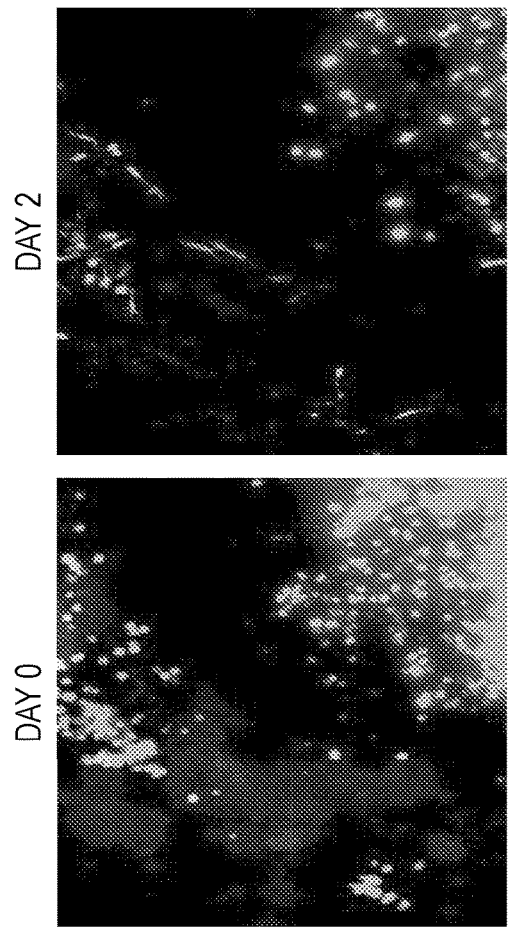
FIG. 10. Anti-tumor effects of therapeutic hMSCs delivered in fibrin against established tumors. (A) The efficacy of hMSC-sTR encapsulated in fibrin for treatment solid GBM was determine using 3-D GBM spheroids and levitation culture. Magnetically labeled human GBM spheroids expressing mCherry and firefly luciferase were cultured with magnetically labeled hMSC-sTR or hMSC-GFPRL encapsulated in fibrin. Both cell types were levitated using a magnet placed on the top of the culture dish and tumor spheroid viability was determined using FLuc BLI. (B-C) Representative images and summary graph demonstrating the significant reduction in the viability of human GBM spheroids by hMSC-sTR/fibrin treatment compared to control-treated spheroids. (D) To determine the efficacy of Fibrin-based hMSC delivery on established tumors, U87-mCFL xenografts were created in mice. hMSC-sTR or control hMSC-GFPRL in Fibrin were surgically implanted over each established tumor. (E-F) Serial bioluminescence imaging was used to follow the growth tumors in each treatment group. Significantly smaller tumor volumes were observed in hMSCsTR treated tumors across multiple time points. In all panels, *P<0.01 vs. control and values are mean±SEM.
Figure 10:
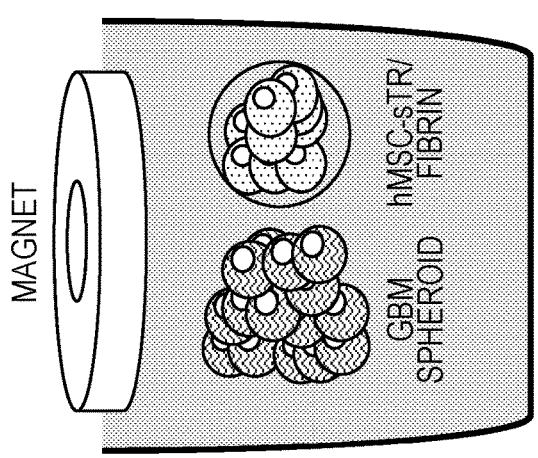
Figure 10:
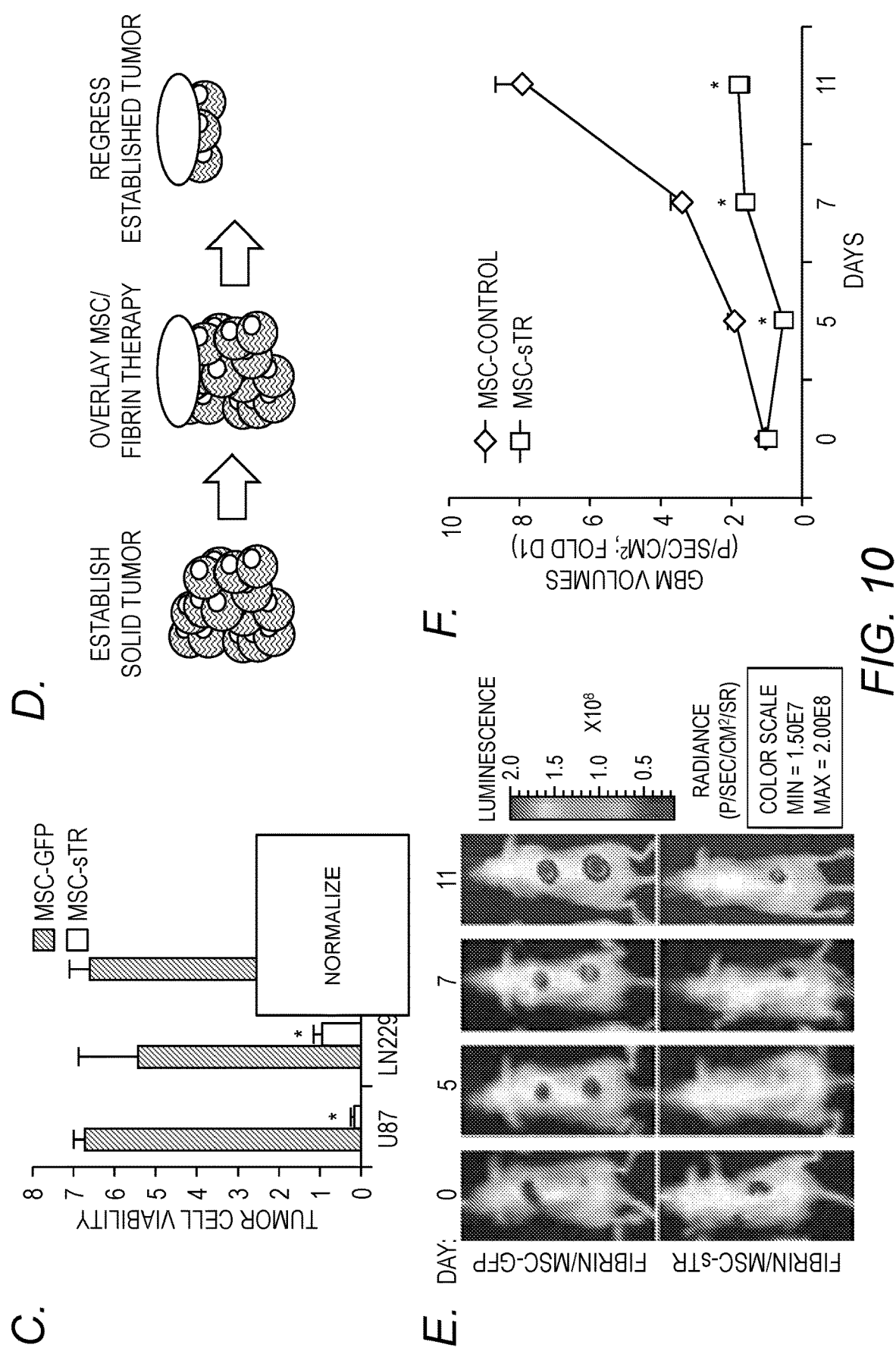

To initially characterize the efficacy cytotoxic hMSC/fibrin therapy for GBM, we used a novel 3-D levitation co-cultured strategy to more accurately mimic in vivo therapy for solid GBM foci (FIG. 10A). hMSC-sTR or hMSC-GFPRLuc were labeled with magnetic material, encapsulated in fibrin, and co-cultured with magnetically-labeled mCherry-luciferase+3-D human GBM spheroids. A magnet was placed over the culture dish to levitate the cells. BLI performed 48 hrs later revealed hMSC-sTR/fibrin reduced the viability of solid GBM spheroids by 92% (U87), 85% (LN229), and 80% (U251) compared to control-treated spheroids (FIG. 10B-10C). These findings suggest hMSC-sTR/fibrin therapy can reduce the viability of solid GBM spheroids.

hMSC/Fibrin Therapy for Solid Tumors.

To study the efficacy of fibrin-based cytotoxic hMSC therapy for established tumors, U87-mCFL cells were xenografted into mice and allowed to grow for 10 days. hMSC-sTR or control hMSC-GFPRLuc were encapsulated in fibrin and surgically implanted over each established tumor (outlined in FIG. 9D). Serial BLI of tumor growth showed hMSC-sTR/fibrin transplant significantly inhibited tumor progression, reducing tumor volume 4.2-fold 11 days post-treatment compared to control-treated animals (FIG. 9E-9F). Together, these findings demonstrate that fibrin-encapsulated hMSC-sTR therapy markedly attenuates the progression of solid tumors.

Intracavity Cytotoxic hMSC/Fibrin Therapy for Post-Surgical Minimal GBM.

Figure 11:
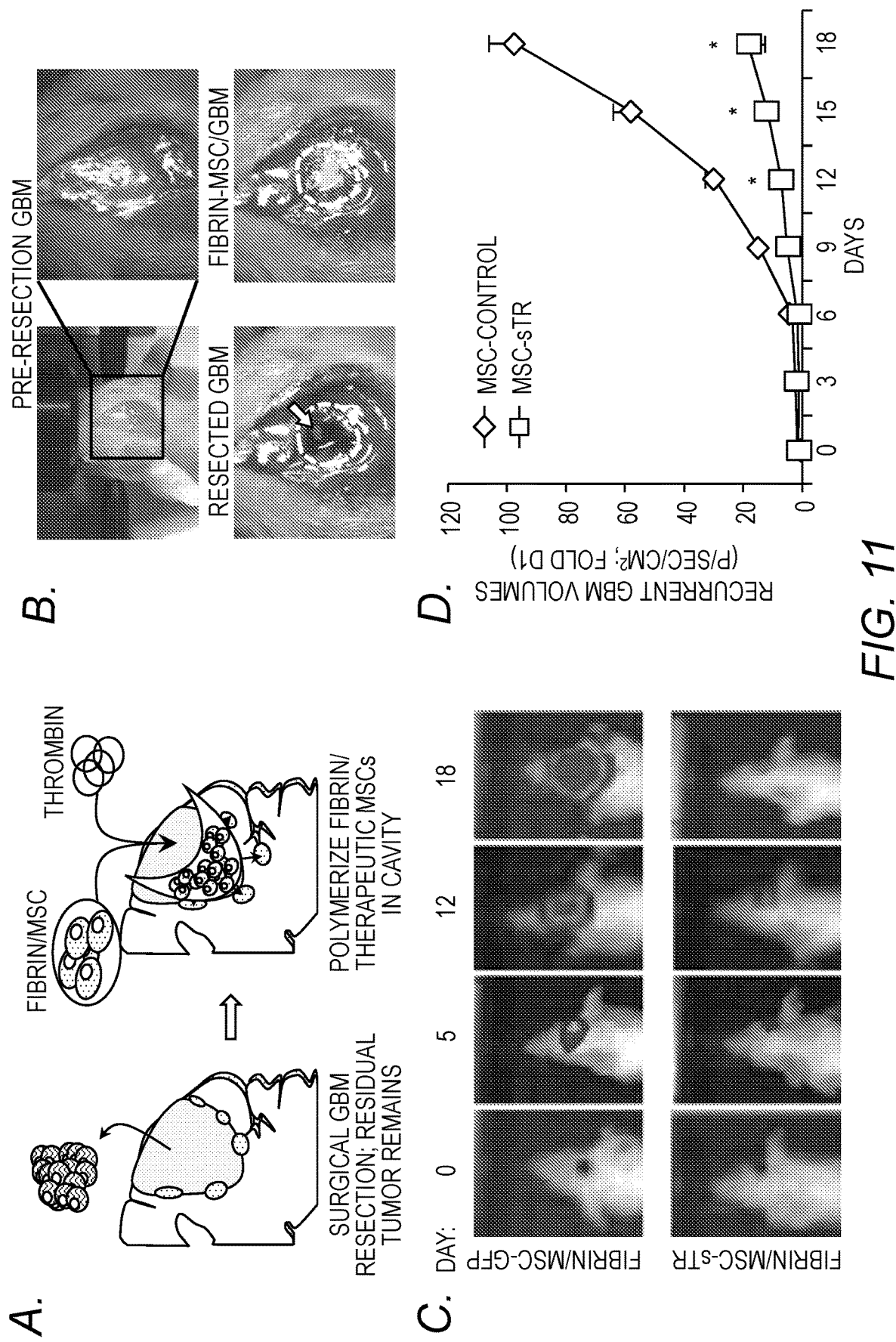
FIG. 11. Cytotoxic hMSCs delivered into the resection cavity infibrin delay re-growth of post-surgical residual GBM. (A) To test the efficacy of fibrin-delivered stem cell therapy for surgically resected GBM, established human U87 GBM were surgically debulked in mice. Therapeutic stem cells were transplanted into the post-operative cavity in fibrin that was polymerized in the cavity by the addition of thrombin. (B) Representative images showing pre-resection mCherry+ GBMs, the post-surgical GBM cavity, and GFP+ hMSC-sTR in fibrin seeded in the resection cavity. The dotted line indicates the resection cavity. The arrowheads indicate residual GBM foci. (C-D) Representative images (C) and summary graph (D) of serial BLI showing a significant reduction in GBM regrowth in hMSC-sTR-treated animals compared to control-treated animals. Significantly smaller tumor volumes were observed in hMSC-sTR-treated tumors across multiple time points. (E) Kaplan-Meyer survival analysis showing the survival of animals with resected GBMs treated with hMSC-sTR therapy or control hMSC-GFPRLuc. Median survival was 36 days for hMSC-sTR treated animals vs. 15 days for control-treated mice. (F) Fluorescent images of post-mortem tissue sections showing the presence of GFP+ hMSCs (green) along the boarder of the recurrent GBM (red). Nuclei were counterstained with Hoechst (blue). In all panels, *P<0.01 vs. control and values are mean±SEM.
Figure 11:
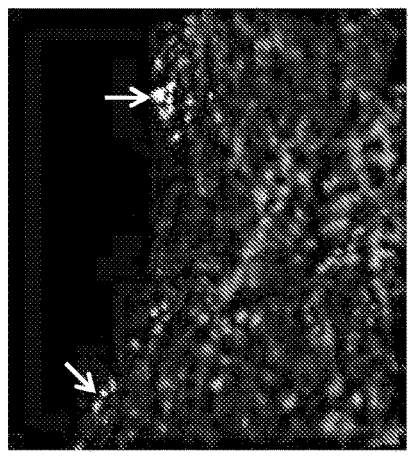
Figure 11:
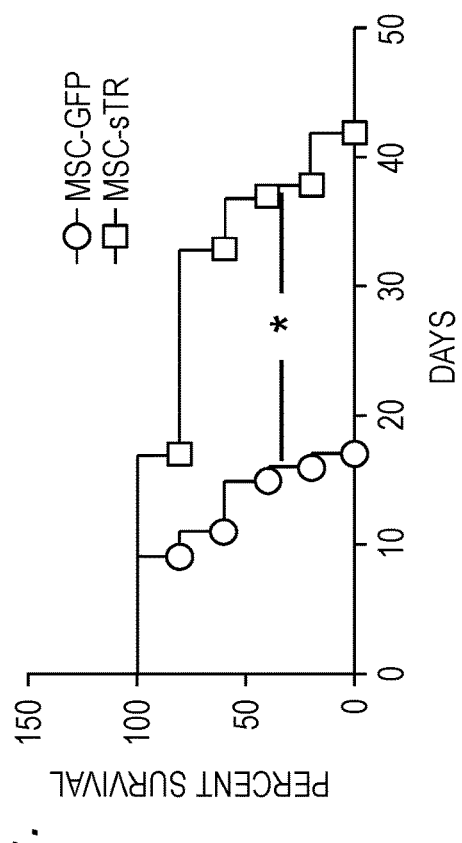

Surgical GBM resection is part of the clinical standard-of-care for human GBM patients. Therefore, we determined the impact of fibrin-encapsulated hMSC-sTR intracavity therapy for post-surgical minimal GBMs. Human GBM cells were xenografted into the parenchyma of mice. 1 week later, the tumors were surgically resected. Cytotoxic hMSCsTR or control hMSC-GFPRLuc were mixed in fibrin, transplanted into the resection cavity, and polymerized by the addition of thrombin (outlined in FIG. 11A). Intraoperative fluorescent imaging was used to reveal the location of the mCherry+ GBM, guide surgical resection, and confirm efficient seeding of hMSC-sTR/fibrin into the resection cavity (FIG. 11B). Serial BLI revealed rapid GBM recurrence in control-treated animals, with tumors increasing 110-fold in 18 days (FIG. 11C-11D). In contrast, hMSC-sTR/fibrin therapy suppressed GBM recurrence 8-fold at 18 days after therapy. Survival analysis revealed the hMSC-sTR/fibrin tumor suppression allowed animals to survive more than 36 days after initial treatment (FIG. 11E). In contrast, control animals succumbed to recurrent GBMs only 15 days after surgery. Post-mortem tissue analysis revealed the presence of hMSC-sTR in the residual GBM microsatellite foci on the boarder of the GBM resection cavity (FIG. 11F).

Taken together, our results strongly suggest that intracavity hMSC-sTR/fibrin therapy is a highly efficacious treatment for post-surgical minimal GBM.

1 Adamson, C. et al. Glioblastoma multiforme: a review of where we have been and where we are going. *Expert Opin Investig Drugs* 18, 1061-1083, doi:10.1517/13543780903052764 (2009).
2 Erpolat, O. P. et al. Outcome of newly diagnosed glioblastoma patients treated by radiotherapy plus concomitant and adjuvant temozolomide: a long-term analysis. *Tumori* 95, 191-197 (2009).
3 Stupp, R. et al. Effects of radiotherapy with concomitant and adjuvant temozolomide versus radiotherapy alone on survival in glioblastoma in a randomised phase II study: 5-year analysis of the EORTC-NCIC trial. *The lancet oncology* 10, 459-466, doi:10.1016/S1470-2045(09)70025-7 (2009).
4 Aboody, K. S., Najbauer, J. & Danks, M. K. Stem and progenitor cell-mediated tumor selective gene therapy. *Gene therapy* 15, 739-752, doi:10.1038/gt.2008.41 (2008).
Ahmed, A. U., Alexiades, N. G. & Lesniak, M. S. The use of neural stem cells in cancer gene therapy: predicting the path to the clinic. *Current opinion in molecular therapeutics* 12, 546-552 (2010).
6 Aboody, K. S. et al. Neural stem cell-mediated enzyme/prodrug therapy for glioma: preclinical studies. *Science translational medicine* 5, 184ra159, doi:10.1126/scitranslmed.3005365 (2013).
7 Hingtgen, S. et al. Real-time multi-modality imaging of glioblastoma tumor resection and recurrence. *Journal of neuro-oncology* 111, 153-161, doi:10.1007/s11060-012-1008-z (2013).
8 Kauer, T. M., Figueiredo, J. L., Hingtgen, S. & Shah, K. Encapsulated therapeutic stem cells implanted in the tumor resection cavity induce cell death in gliomas. *Nat Neurosci* 15, 197-204, doi:10.1038/nn.3019 (2012).
9 Weisel, J. W. Fibrinogen and fibrin. *Advances in protein chemistry* 70, 247-299, doi:10.1016/S0065-3233(05)70008-5 (2005).
Jackson, M. R. Fibrin sealants in surgical practice: An overview. *American journal of surgery* 182, 1S-7S (2001).
11 Kassam, A. et al. Use of Tisseel fibrin sealant in neurosurgical procedures: incidence of cerebrospinal fluid leaks and cost-benefit analysis in a retrospective study. *Neurosurgery* 52, 1102-1105; discussion 1105 (2003).
12 Fraioli, R. E., Hirsch, B. E. & Kassam, A. B. Fibrin sealant for control of cerebrospinal fluid otorrhea. *American journal of otolaryngology* 29, 135-137, doi: 10.1016/j.amjoto.2007.04.002 (2008).
13 Janmey, P. A., Winer, J. P., Murray, M. E. & Wen, Q. The hard life of soft cells. *Cell Motil Cytoskeleton* 66, 597-605, doi:10.1002/cm.20382 (2009).
14 Rowe, S. L., Lee, S. & Stegemann, J. P. Influence of thrombin concentration on the mechanical and morphological properties of cell-seeded fibrin hydrogels. *Acta Biomater* 3, 59-67, doi:10.1016/j.actbio.2006.08.006 (2007).
15 Haney, M. J. et al. Specific transfection of inflamed brain by macrophages: a new therapeutic strategy for neurodegenerative diseases. *PloS one* 8, e61852, doi:10.1371/journal.pone.0061852 (2013).
16 Hingtgen, S. D., Kasmieh, R., van de Water, J., Weissleder, R. & Shah, K. A novel molecule integrating therapeutic and diagnostic activities reveals multiple aspects of stem cell-based therapy. *Stem Cells* 28, 832-841, doi:10.1002/stem.313 (2010).
17 Ehtesham, M. et al. The use of interleukin 12-secreting neural stem cells for the treatment of intracranial glioma. *Cancer research* 62, 5657-5663 (2002).

Example 4: Transplanting Cytotoxic Stem Cells in GELFOAM® Scaffolds

Figure 12:
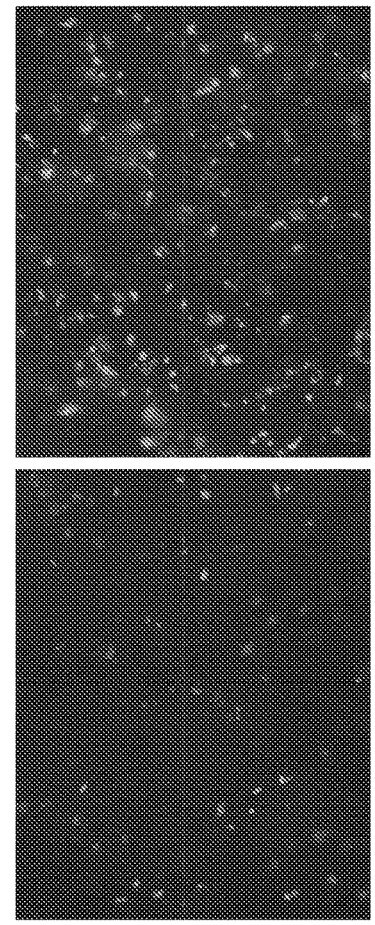
FIG. 12. In vitro characterization of human neural stem cells (NSCs) on Gelfoam). (A) White light and fluorescent images of human NSCs grown on GELFOAM® 0 and 3 day after seeding. (B) Summary data showing the growth of human NSCs grown on GELFOAM®. (C) Fluorescent imaging of a cross-section of GELFOAM® loaded with human NSCs (red) to determine the distribution of cells loaded on the scaffolds. Imaging showed greater numbers of NSCs attached to the boarder of GELFOAM® (indicated by arrows), while the core of the GELFOAM® contained fewer NSCs. These results suggest NSCs attach to GELFOAM® and proliferate in the matrix.
Figure 12:
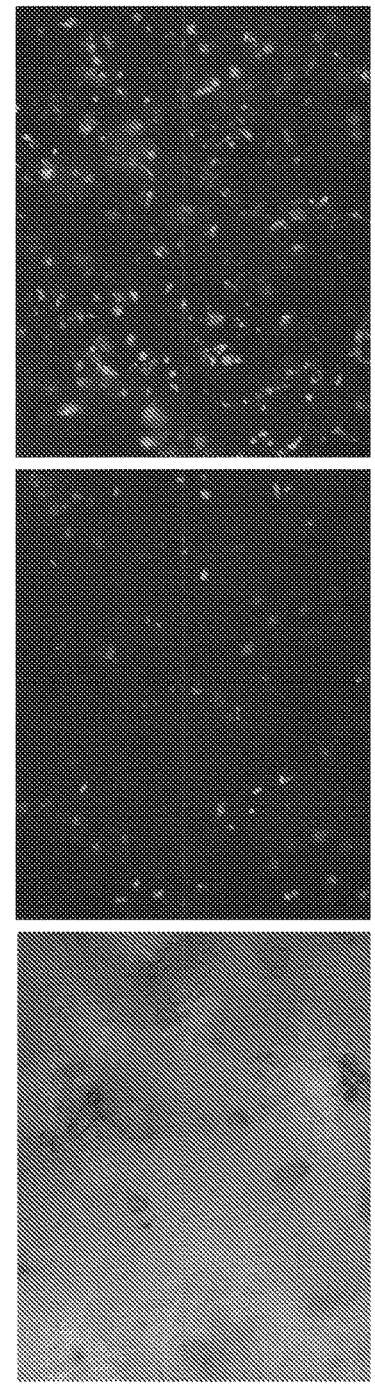

Characterization of human neural stem cells (NSCs) incorporated into GELFOAM® (Pharmacia & Upjohn Co., Kalamazoo, Mich.) was performed in vitro. The cells were loaded by pipetting a concentrated NSC solution onto the fibers, which were incubated for 1-8 hrs to allow attachment. As shown in FIG. 12, greater numbers of NSCs attached to the boarder of gelfoam, while the core of the gelfoam contained fewer NSCs. These results suggest NSCs attach to gelfoam and proliferate in the matrix.

In vitro 3-dimensional migration analysis was also performed, as show in FIG. 13. Culture plates are filled with agar and mCherry+ GBM cells are implanted to created a 3-D tumor. Three days later, a portion of the tumor is removed to mimic a resection cavity. GELFOAM® bearing GFP+ NSCs is then seeded into the cavity. The gel was cut into cross sections 1 and 7 days after seeding, and fluorescent imaging was used to visualize the co-localization of the GFP+ NSCs with mCherry+ GBM. We found a large number of NSCs had migrated from the GELFOAM® scaffold, through the agar, and populated the GBM (red) in the day 7 sections. These migratory cells are indicated by arrowheads. These results suggest NSCs are capable of migrating from the GELFOAM®, homing to GBM foci.

Figure 14:
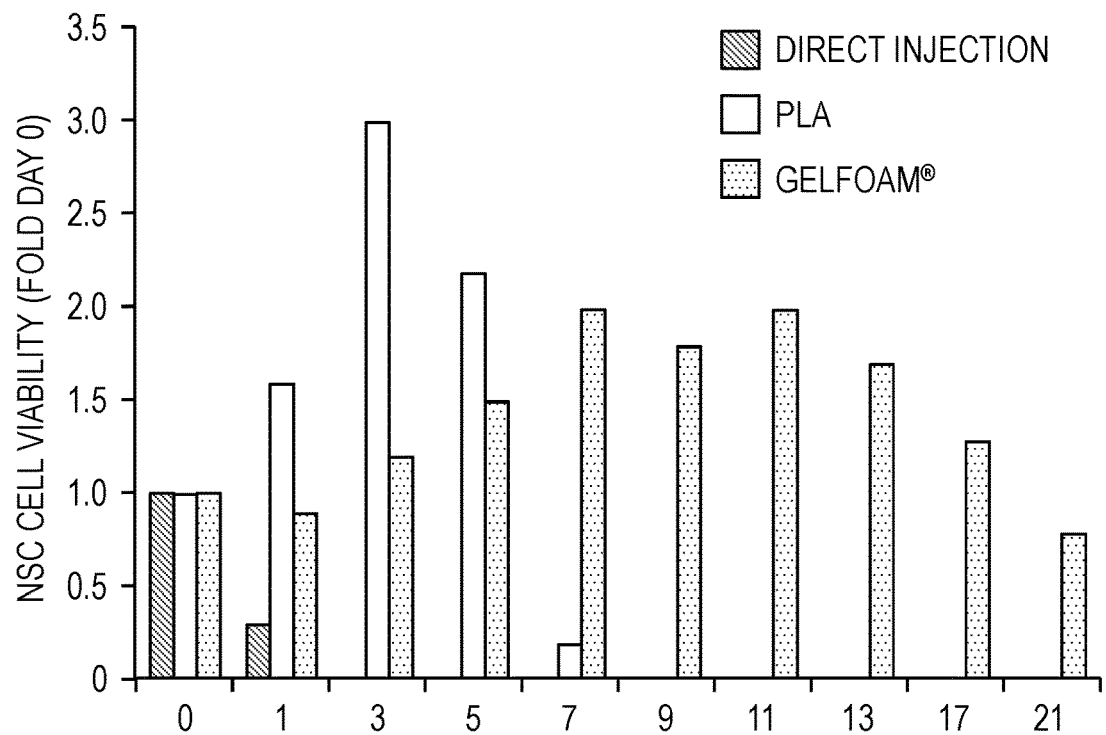
FIG. 14. In vivo persistence of NSC transplanted into the GBM resection cavity on different scaffolds. Human U87 GBM cells were surgically resected in mice to create a resection cavity. Luciferase+ NSCs were seeded on PLA or GELFOAM® and seed into the resection cavity. NSCs were directly injected in suspension in an additional group. Serial bioluminescence imaging was used to track the persistence of the NSCs in the surgical resection cavity. It was found that directly injected NSCs were cleared in only 4 days. NSCs delivered on PLA initially and persisted for 8 days, NSCs delivered on GELFOAM® also initially proliferated and persisted for greater than 21 days. These data suggest that NSCs persist the longest in the GBM resection cavity on GELFOAM® scaffolds, and this strategy will likely achieve the greatest treatment durability.

In vivo persistence of NSC transplanted into the GBM resection cavity was compared on different scaffolds (FIG. 14). Human U87 GBM cells were surgically resected in mice to create a resection cavity. Luciferase+ NSCs were seeded on PLA or GELFOAM® and seed into the resection cavity. NSCs were directly injected in suspension in an additional group. Serial bioluminescence imaging was used to track the persistence of the NSCs in the surgical resection cavity. It was found that directly injected NSCs were cleared in only 4 days. NSCs delivered on PLA initially and persisted for 8 days, whereas NSCs delivered on GELFOAM® also initially proliferated and persisted for greater than 21 days. These data suggest that NSCs persist the longest in the GBM resection cavity on GELFOAM® scaffolds, and this strategy will likely achieve the greatest treatment durability.

Figure 15:
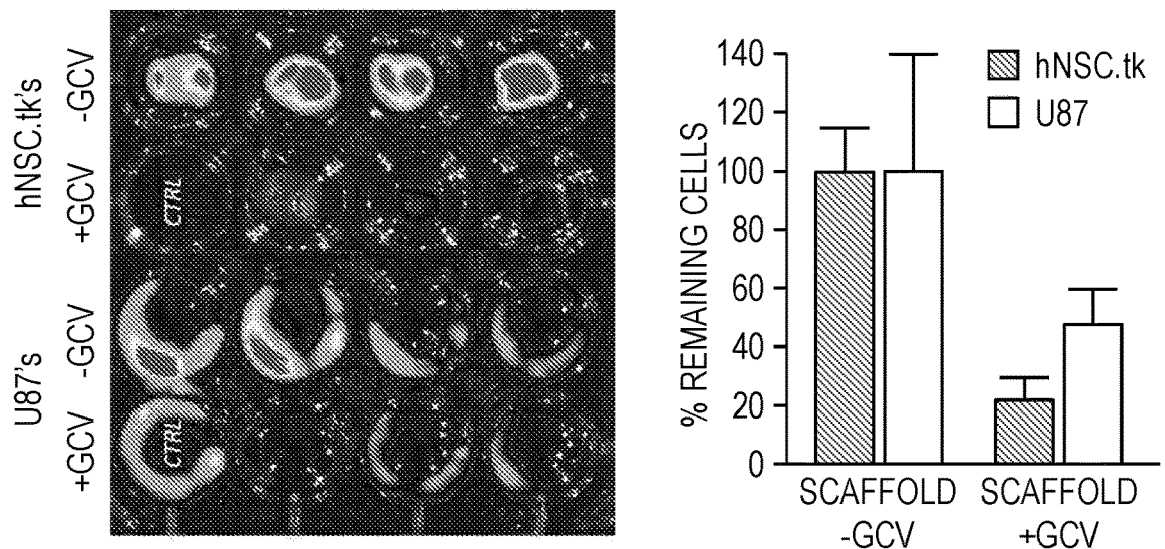
FIG. 15. NSC prodrug/enzyme therapies on Gelfoam® scaffolds kill GBM cells in culture. Human NSCs were engineered to express thymidine kinase (NSC-TK). The NSC-TK were loaded on Gelfoam® and seeded in co-culture assays with human U87 GBM cells. The wells were treated with ganciclovir (GCV) pro-drug to initiate therapy or saline as a control. Cell viability assays showed GCV treatment reduced the viability of both the U87 GBM cells and the NSCs.

As shown in FIG. 15, NSC prodrug/enzyme therapies on GELFOAM® scaffolds kill GBM cells in culture. Human NSCs were engineered to express thymidine kinase (NSC- TK). The NSC-TK were loaded on GELFOAM® and seeded in co-culture assays with human U87 GBM cell. The wells were treated with ganciclovir (GCV) pro-drug to initiate therapy or saline as a control. Cell viability assays showed GCV treatment reduced the viability of both the U87 GBM cells and the NSCs. These data suggest GELFOAM®/NSC-TK therapy has anti-GBM effects.

Figure 16:
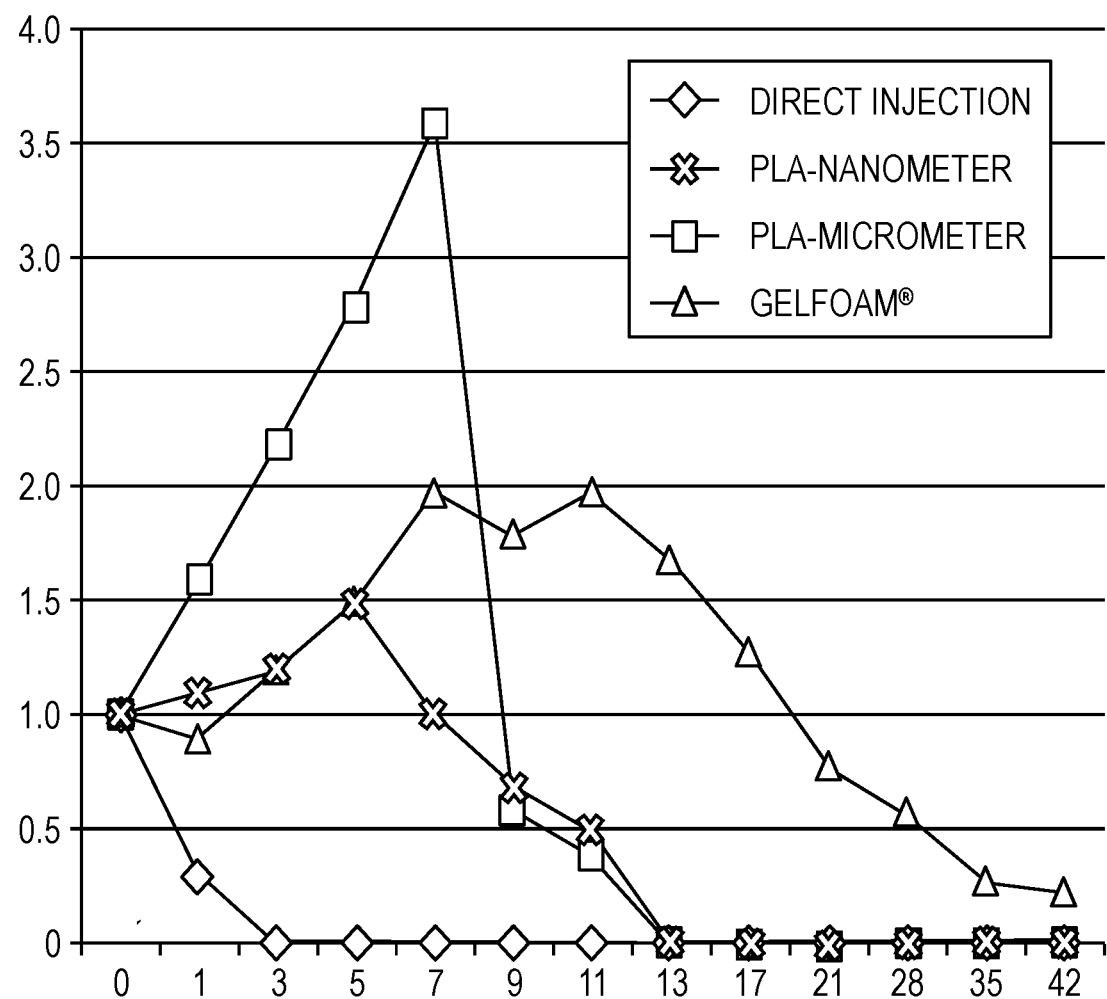
FIG. 16. NCSs persist in vivo when delivered with Gelfoam® for more than 40 days. The persistence (quantity) of NSCs is on the vertical axis. Time in days is across the horizontal axis. Shown are: 1. Direct injection (NSCs in solution delivered in a needle); 2. PLA-nanometer (NSCs on a nanometer electrospun PLA); 3. PLA-micrometer (NSCs on thick micrometer PLA); and 4. GELFOAM® (NSCs on GELFOAM®).

In summary, GELFOAM® showed an unexpected and dramatic increase in the persistence of human NSCs in the resection cavity. This was the case even when compared to electrospun PLA scaffolds having fiber diameters on the nanometer or micrometer scales (FIG. 16).

Example 5: Use of iNSC-Containing Gelatin Sponge Vehicle for Treatment of Brain Cancer A patient is diagnosed with brain cancer (e.g., glioblastoma), and surgery is scheduled for removing the tumor soon thereafter (e.g., within one, two or three weeks). A skin punch is taken from the patient to obtain skin fibroblast cells. The cells are transdifferentiated as taught herein into induced neural stem cells and also loaded with a therapeutic agent and/or a reporting molecule. The loaded iNSCs are incorporated onto/into a sterile gelatin sponge (e.g., GELFOAM®). During surgery and after removal of the tumor, the iNSC-containing gelatin sponge is placed into the cavity where the tumor had been removed. The iNSCs migrate out of the sponge toward residual cancer cells and deliver their therapeutic agent/reporting molecule payload, killing the cancer cells.

The foregoing is illustrative of the present invention, and is not to be construed as limiting thereof. The invention is defined by the following claims, with equivalents of the claims to be included therein.

That which is claimed is:

1. A method of forming a scaffold comprising stem cells, wherein said stem cells are mammalian neural stem cells, wherein said stem cells are loaded with a therapeutic agent, and optionally wherein said stem cells are also loaded with a reporter molecule, said method comprising:
    providing a polymerizable and/or crosslinkable material that is not gelatin, wherein said material further comprises crosslinked gelatin, wherein said crosslinked gelatin is not collagen, optionally wherein the material is sterile,
    mixing said polymerizable and/or crosslinkable material with said stem cells to form a mixture of said material and said stem cells, and
    polymerizing and/or crosslinking said material of said mixture,
    to thereby form said scaffold comprising said stem cells,
    wherein said scaffold is biocompatible and wherein said scaffold allows the stem cells to migrate away from the scaffold and towards a cancerous or damaged tissue.

2. The method of claim 1, wherein said stem cells are induced neural stem cells.

3. The method of claim 1, wherein said stem cells are induced neural stem cells derived from skin fibroblast cells.

4. The method of claim 1, wherein said therapeutic agent is an enzyme useful for enzyme/prodrug therapy.

5. The method of claim 1, wherein said stem cells are human neural stem cells.

6. The method of claim 1, wherein the polymerizing and/or crosslinking are performed in situ during intracavity administration after surgical removal of a brain tumor.

7. The method of claim 1, wherein the scaffold is administered to line the walls of a resection cavity of a brain tumor.

8. The method of claim 1, wherein said polymerizable and/or crosslinkable material comprises fibrinogen and wherein said polymerizing and/or crosslinking is carried out by adding thrombin to said mixture.

9. The method of claim 1, wherein said polymerizing and/or crosslinking is carried out by adding a chemical crosslinking agent.

\* \* \* \* \*

UNITED STATES PATENT AND TRADEMARK OFFICE
CERTIFICATE OF CORRECTION

PATENT NO. : 11,027,047 B2
APPLICATION NO. : 15/559596
DATED : June 8, 2021
INVENTOR(S) : Hingtgen et al.

It is certified that error appears in the above-identified patent and that said Letters Patent is hereby corrected as shown below:

In the Specification

Column 3, Line 12: Please correct "INSCs" to read -- iNSCs --

Column 7, Line 2: Please correct "Gelfoam)." to read -- Gelfoam®. --

Column 14, Line 52: Please correct "INSCs" to read -- iNSCs --

Column 15, Line 30: Please correct "100 dl/well" to read -- 100 µl/well --

Column 16, Line 34: Please correct "INSC" to read -- iNSC --

Column 16, Line 53: Please correct "150 dl" to read -- 150 µl --

Column 18, Line 29: Please correct "500 m" to read -- 500 µm --

Column 22, Line 38: Please correct "IVIS'" to read -- IVIS® --

Column 22, Line 41: Please correct "IVIS'" to read -- IVIS® --

Column 22, Line 50: Please correct "1 g/ml" to read -- 1 µg/ml --

Column 23, Line 26: Please correct "In Vive" to read -- In Vivo --

Column 23, Line 48: Please correct "IVIS'" to read -- IVIS® --

Column 24, Line 23: Please correct "IVIS'" to read -- IVIS® --

Signed and Sealed this
Fifth Day of October, 2021

Drew Hirshfeld
*Performing the Functions and Duties of the
Under Secretary of Commerce for Intellectual Property and
Director of the United States Patent and Trademark Office*